(12) United States Patent
Morrow et al.

(10) Patent No.: US 7,893,041 B2
(45) Date of Patent: Feb. 22, 2011

(54) OLIGOSACCHARIDE COMPOSITIONS AND USE THEREOF IN THE TREATMENT OF INFECTION

(75) Inventors: Ardythe L. Morrow, Cincinnati, OH (US); David S. Newburg, Newtonville, MA (US); Guillermo M. Ruiz-Palacios, Mexico City (MX)

(73) Assignees: Children's Hospital Medical Center, Cincinnati, OH (US); Instituto Nacional De Ciencias Medicas Y Nutricion, Mexico, D.F. (MX); University of Massachusetts, Boston, MA (US)

( * ) Notice: Subject to any disclaimer, the term of this patent is extended or adjusted under 35 U.S.C. 154(b) by 877 days.

(21) Appl. No.: 10/581,759

(22) PCT Filed: Dec. 6, 2004

(86) PCT No.: PCT/US2004/040882

§ 371 (c)(1),
(2), (4) Date: Jul. 26, 2007

(87) PCT Pub. No.: WO2005/055944

PCT Pub. Date: Jun. 23, 2005

(65) Prior Publication Data

US 2007/0275881 A1 Nov. 29, 2007

Related U.S. Application Data

(60) Provisional application No. 60/527,591, filed on Dec. 5, 2003.

(51) Int. Cl.
*A61K 31/702* (2006.01)
*A61K 38/38* (2006.01)

(52) U.S. Cl. .............. 514/62; 514/8; 514/53; 514/61

(58) Field of Classification Search ........ None
See application file for complete search history.

(56) References Cited

U.S. PATENT DOCUMENTS

| | | | | |
|---|---|---|---|---|
| 5,470,843 A | * | 11/1995 | Stahl et al. | 514/61 |
| 5,474,986 A | * | 12/1995 | Magnusson et al. | 514/53 |
| 5,892,070 A | | 4/1999 | Prieto et al. | 800/2 |
| 5,919,913 A | | 7/1999 | Nuyens et al. | 530/395 |
| 6,045,854 A | * | 4/2000 | Prieto et al. | 426/658 |
| 6,146,670 A | | 11/2000 | Prieto et al. | 426/72 |
| 6,291,435 B1 | * | 9/2001 | Yanmaele et al. | 514/25 |
| 2002/0019991 A1 | * | 2/2002 | Prieto et al. | 800/3 |
| 2002/0058313 A1 | | 5/2002 | Renkonen et al. | 435/105 |

FOREIGN PATENT DOCUMENTS

| | | |
|---|---|---|
| WO | WO 95/24495 | 9/1995 |
| WO | WO 99/56754 | 11/1999 |

OTHER PUBLICATIONS

Jiang, Z. et al "Prevalence of enteric pathoges among international travelers . . . " J. Infect. Dis. (2002) vol. 185, pp. 497-502.*
Pradel, N. et al "Prevalence and characterization of shiga toxin . . . " J. Clin. Microbiol. (2000) vol. 38, No. 3, pp. 1023-1031.*
Yolken, R. et al "Human milk mucin inhibits rotovirus . . . " J. Clin. Invest. (1992) vol. 90, pp. 1984-1991.*
Wilson, N. et al "Glycoproteomics of milk . . . " J. Proteome Res. (2007) vol. 7, pp. 3687-3696.*
Prestwich, G. et al "Controlled chemical modification of hyaluronic acid . . . " J. Controlled Release (1998) vol. 53, pp. 93-103.*
Cregg et al., "Recombinant protein expression in Pichia pastoris" Mol. Biotechnol. 16:23-52, 2000.
Dai et al., "Role of oligosaccharides and glycoconjugates in intestinal host defense" J. Ped. Gastroenterol vol. 30(2):S23-S33, 2000.
Wu et al., "Identification and characterization of GDP-D-mannose 4,6-Dehydratase . . . " Biochem. Biophys. Res. Comm. 285:364-371, 2001.

* cited by examiner

*Primary Examiner*—Leigh C Maier
(74) *Attorney, Agent, or Firm*—Occhiuti Rohlicek & Tsao LLP

(57) ABSTRACT

Oligosaccharides and oligosaccharides linked to backbones such as proteins, methods for making such oligosaccharides and methods for using them to treat and/or prevent various disorders are described.

20 Claims, 10 Drawing Sheets

| Cells | Pathogenic | | | | | Non Pathogenic | |
|---|---|---|---|---|---|---|---|
| | UEA 1 | INN 287IP | INN 84SP | INN 166IP | INN 10SP | INN 50SP | INN 57SP |
| FUT1 (α1,2) | 3+ | 2+ | 2+ | 1+ | 2+ | 0 | 0 |
| FUT3 (α1,3) | 0 | 0 | 0 | 0 | 0 | 0 | 0 |
| FUT4 (α1,3 and α1,4) | 0 | 0 | 0 | 0 | 0 | 0 | 0 |
| Parental CHO | 0 | 0 | 0 | 0 | 0 | 0 | 0 |

| Days After Infection | Transgenic (FUT1) | | | Non-Transgenic |
|---|---|---|---|---|
| | Campylobacter Inoculum (CFU/ml) | | | |
| | x10$^4$ | x10$^8$ | X10$^9$ | Controlx10$^8$ |
| 1 | 40 | 30 | 90 | 100 |
| 3 | 40 | 60 | 50 | 100 |
| 5 | 10 | 40 | 20 | 67 |
| 7 | 0 | 0 | 0 | 70 |
| 9 | 0 | 10 | 20 | 67 |
| 11 | 0 | 0 | 0 | 70 |
| 13 | 0 | 0 | 0 | 78 |
| 15 | 0 | 0 | 0 | 88 |

FIG. 10B

OLIGOSACCHARIDE COMPOSITIONS AND USE THEREOF IN THE TREATMENT OF INFECTION

This application is a U.S. National Phase of PCT application serial number PCT/US2004/040882, filed Dec. 6, 2004, which claims priority under 35 U.S.C. §119(e)(1) from U.S. application Ser. No. 60/527,591, filed Dec. 5, 2003, the entire contents of both of which are hereby incorporated by reference.

BACKGROUND

Consumption of human milk is one of the most cost-effective strategies known to medicine for protecting infants against morbidity and mortality due to infectious disease. Human milk may be considered a natural and efficacious "nutriceutical," i.e., a model food that conveys immunologic benefits. Protection against infectious diseases occurs through a variety of complementary mechanisms found in human milk, including oligosaccharides and their related glycoconjugates. Significantly enhanced immunologic protection by breastfeeding has been demonstrated for diarrheal diseases, respiratory tract illnesses, bacteremia, meningitis, and necrotizing enterocolitis. Protection by breastfeeding is especially efficacious against diarrheal disease.

Milk oligosaccharide structures are thought to serve as receptor analogs that can inhibit pathogen binding to host ligands (1-3). It appears that certain $\alpha$1,2-linked fucosylated oligosaccharides in human milk are associated with protection against diarrhea due to *campylobacter* (2,4), caliciviruses (3-5), and stable toxin (ST)-associated *Escherichia coli* (1,6,7).

Oligosaccharides and their related glycoconjugates are major components of the innate defense system found in human milk. Oligosaccharides, which vary from 3 to 32 sugars in size, constitute the third-most common solid component of human milk after lactose and lipid, but their role is immunologic rather than nutritive. Oligosaccharides appear to have several different immunologic functions. Several types of oligosaccharides, including fucosyloligosaccharides, sialylated oligosaccharides, and non-fucosylated non-sialylated oligosaccharides in human milk, have prebiotic properties, i.e., selective stimulation of the growth of beneficial bacteria in the intestine. Importantly, protection against specific pathogens has been described for both fucosylated and sialylated human milk oligosaccharides (5, 6, 24, 27, 28). Both the fucosylated oligosaccharides and the sialylated oligosaccharides may have structural homology to cell receptors for enteropathogens and inhibit pathogen binding by blocking binding to relevant cell receptors (24, 29, 30). Certain pathogens are thought to bind to sialic acid- and fucose-containing receptors, including enteropathogenic *Escherichia coli* (EPEC), rotavirus, *Haemophilus influenzae* and other pathogens (30-33). In addition to the unbound oligosaccharides, protection by glycoconjugated substances in human milk has been demonstrated by in vitro studies and/or animal models against labile toxin and cholera toxin, heat-stable enterotoxin of *E. coli* (ETEC), *campylobacter*, shiga toxin, *Streptococcus pneumoniae* and rotavirus (16, 17, 24, 34). Lactadherin, a 46-kDa glycoprotein, has been found to vary in concentration in human milk, and significant protection against symptomatic rotavirus infection is associated with increasing concentrations of lactadherin in maternal milk (34).

The fucose terminus of oligosaccharide structures may be connected by an $\alpha$1,2 linkage catalyzed by a fucosyltransferase produced by the secretor gene (FUT2) or by the fucosyltransferase I gene (FUT1), or by an $\alpha$1,3 or $\alpha$1,4 linkage catalyzed by fucosyltransferases produced by the Lewis gene (FUT3) family. Polymorphisms of the secretor and Lewis genes are known to determine expression of the Lewis blood group type, fucosylated oligosaccharide patterns in human milk, and histo-blood group antigens on human epithelial cell surfaces (21, 22, 35). Some individuals are non-secretors (i.e., homozygous recessive for the secretor gene) who do not synthesize $\alpha$1,2-linked fucosyloligosaccharides in their secretions. In Indo-European and African populations, the prevalence of non-secretors is approximately 20%, while in some other populations, such as Mexicans of indigenous ancestry, non-secretors are much less common (36-38). In certain cases it has been shown that this heterogeneity of expression is associated with differential risk of infectious diseases in individuals and populations (5, 6, 28, 37, 39-44). Moreover, variation in concentration of protective oligosaccharides in human milk may result in breastfed infants with differing levels of protection against specific infectious diseases (21, 22, 36, 39, 45).

The most common oligosaccharides of human milk include four $\alpha$1,2-linked fucosylated oligosaccharides (lacto-N-fucopentaose I [LNF-I], 2-fucosyllactose [2'-FL], lacto-N-difucohexaose I [LDFH-I] and lactodifucotetraose [LDFT]); three fucosylated oligosaccharides that lack 2-linked fucose (lacto-N-fuco-pentaose II [LNF-II], 3-fucosyllactose [3-FL], and lacto-N-fucopentaose III [LNF-III]); and their two precursors (lacto-N-tetraose [LNT] and lacto-N-neotetraose [LNneoT]). These nine oligosaccharides are homologs of the Lewis histo-blood group antigens, respectively: H-1, H-2, Le$^b$, Le$^y$, Le$^a$, Le$^x$, type 1 precursor, and type 2 precursor. The most commonly occurring specific $\alpha$1,2-linked fucosylated oligosaccharide in human milk is 2'-FL (H-2 epitope). Comparing the composition of milks from many different mammalian species, 2'-FL is also the most conserved oligosaccharide structure, suggesting its importance in evolutionary biology (46). 2'-FL is absent, however, from the milk of some species, including cow's milk.

SUMMARY

The invention features a pharmaceutical composition comprising a molecule comprising a fucose group in an $\alpha$1,2 linkage, $\alpha$1,3 linkage, or $\alpha$1,4 linkage to a galactose group and a pharmaceutically acceptable carrier. The fucose can be is contained within an LNF-I group, an 2'FL group, an LDFH-I group or a LDFT group. In some situations the molecule is a glycan, a glycolipid, a glycoprotein, a glycosaminoglycan or a mucin. Thus, the fucose group can be directly or indirectly linked to a protein. The protein or other backbone molecule can contain at least two (three or four) different groups selected from an LNF-I group, and 2'FL group, an LDFH-I group and a LDFT group. The protein or other backbone molecule can bear multiple copies of two or more different groups. The composition does not contain a mammalian milk (e.g., it does not contain human milk).

The compositions can be used as a probiotic agent, i.e., an indigestible agent which induces or promotes colonization of the gut by beneficial microorganisms, e.g., bacteria that improve health or prevent disease.

In another aspect the invention features a pharmaceutical composition comprising a purified protein modified to include at least two (three, four, five, six, seven, eight, nine, ten or more) different groups selected from:

2'-Fucosyllactose;
Lacto-N-fucopentaose I;
Lacto-N-fucopentaose II;
3'-Fucosyllactose;
Lacto-N-fucopentaose II;
Lacto-N-difacohexaose I;
Lactodifacotetraose;
LactoN-tetraose;
LactoN-neotetraose;
3'-Sialyllactose;
3'-Sialyllactosamine;
6'-Sialyllactose;
6'-Sialyllactosamine;
Sialyllacto-N-neotetraose c;
Monosialyllacto-N-hexaose;
Disialyllacto-N-hexaose I;
Monosialyllacto-N-neohexaose I;
Monosialyllacto-N-neohexaose II
Disialyllacto-N-neohexaose
Disialyllacto-N-tetraose;
Disialyllacto-N-hexaose II;
Sialyllacto-N-tetraose a;
Disialyllacto-N-hexaose I;
Sialyllacto-N-tetraose b;
3'-Sialyl-3-fucosyllactose;
Disialomonofucosyllacto-N-neohexaose;
Monofucosylmonosialyllacto-N-octaose (sialyl Lea);
Sialyllacto-N-fucohexaose II;
Disialyllacto-N-facopentaose II; and
Monofucosyldisialyllacto-N-tetraose.

The protein can be modified to contain multiple copies (two, three, fours, five, six, seven, eight, nine, 10, 15, 20, 25 or more) of each of the different groups. The protein itself can be, for example a human milk protein (e.g., κ-casein, α-lactalbumin, lactoferrin, bile salt-stimulated lipase, lysozyme, serum albumin, folate-binding protein, haptocorrin, lipoprotein lipase, glycosaminoglycan, mucin, lactoperoxidase, or amylase) or some other protein, e.g., BSA. The composition is most often a synthetic composition that is not a mammalian milk, although in use it might be mixed with a mammalian milk such as cows milk or human milk. The composition can contain: at least one vitamin; at least one mineral; at least one edible fat; and other nutritional components.

The invention also includes a pharmaceutical composition comprising a purified protein modified to include at least two different groups selected from:
2'-Fucosyllactose;
Lacto-N-fucopentaose I;
Lacto-N-fucopentaose II;
3'-Fucosyllactose;
Lacto-N-fucopentaose II;
Lacto-N-difucohexaose I;
Lactodifucotetraose; and
2'-FLNac, wherein the protein is not modified to contain any other oligosaccharides.

In another aspect the invention includes a synthetic nutritional composition comprising a glycan, a glycolipid, a glycoprotein, a glycosaminoglycan or a mucin that comprises at least two different groups selected from an LNF-I group, and 2'FL group, an LDFH-I group and a LDFT group. The molecule can include at three different groups selected from an LNF-I group, an 2'FL group, an LDFH-I group and a LDFT group and can include multiple copies (1, 2, 3, 4, 5, 6, 7, 8, 9, 10 or more) of the same group.

The invention includes a synthetic nutrition composition comprising a purified protein modified to include at least two (3, 4, 5, 6, or 7 or more) groups selected from: a Lacto-N-fucopentaose I group, a Lacto-N-fucopentaose II group, a 2-Fucosyllactose group, a 3-Fucosyllactose group, a Lacto-N-fucopentaose II group, a Lacto-N-difucohexaose I group, and a Lactodifucotetraose group.

The invention includes a synthetic nutrition composition comprising a purified protein modified to include at least two (3, 4, 5, 6, or 7 or more) groups selected from:
Lacto-N-fucopentaose I;
Lacto-N-fucopentaose II;
3'-Fucosyllactose;
Lacto-N-fucopentaose II;
Lacto-N-difucohexaose I;
Lactodifucotetraose;
LactoN-tetraose;
LactoN-neotetraose;
3'-Sialyllactose;
3'-Sialyllactosamine;
6'-Sialyllactose;
6'-Sialyllactosamine;
Sialyllacto-N-neotetraose c;
Monosialyllacto-N-hexaose;
Disialyllacto-N-hexaose I;
Monosialyllacto-N-neohexaose I;
Monosialyllacto-N-neohexaose II
Disialyllacto-N-neohexaose
Disialyllacto-N-tetraose;
Disialyllacto-N-hexaose II;
Sialyllacto-N-tetraose a;
Disialyllacto-N-hexaose I;
Sialyllacto-N-tetraose b;
3'-Sialyl-3-fucosyllactose;
Disialomonofucosyllacto-N-neohexaose;
Monofucosylmonosialyllacto-N-octaose (sialyl Lea);
Sialyllacto-N-fucohexaose II;
Disialyllacto-N-fucopentaose II; and
Monofucosyldisialyllacto-N-tetraose.

In another aspect the invention features a method for treating or reducing the risk of infection (e.g., a respiratory or enteric infection such as infection by *V. cholerea* or *C. jejuni*), the method comprising administering (to an infant, child or adult) a composition comprising a molecule comprising a fucose group in an α1,2 linkage to a galactose group wherein said composition is not a mammalian milk. Thus, any of the pharmaceutical compositions noted herein can be administered in this method.

The invention also features a method for reducing the risk of enteric disease in a patient, the method comprising: (a) identifying the two most prevalent agents capable of causing enteric disease in the geographic location of the patient; (b) administering to the patient a composition comprising a molecule comprising a first glycan which interferes with the binding to epithelial cells of the first of the two most prevalent agents and a second glycan which interferes with the binding to epithelial cells of the second of the two most prevalent agents wherein said composition is not breast milk.

The invention also features a method for reducing the risk of enteric disease in a patient, the method comprising: (a) identifying the two most prevalent agents capable of causing enteric disease in the geographic location of the patient; (b) administering to the patient composition comprising: i) a first molecule comprising a first glycan which interferes with the binding to epithelial cells of the first of the two most prevalent agents; and ii) a second molecule comprising a glycan which interferes with the binding to epithelial cells of the second of the two most prevalent agents; wherein the composition is not breast milk.

The invention also includes a yeast cell harboring a recombinant vector comprising a nucleotide sequence encoding GDP-mannose 4, 6 dehydratase and a nucleotide sequence encoding GDP-L-fucose synthetase. The yeast cell can further harbor a nucleic acid molecule encoding a GDP-fucose/ GMP antiporter fusion protein (e.g., a fusion protein that comprises a golgi-membrane location sequence (e.g., yeast Vrg4p).

Also within the invention is an isolated nucleic acid molecule encoding a fusion protein comprising at least a first portion and a second portion, the first portion comprising the active domain of a GDP-fucose/GMP antiporter and the second portion comprising a golgi localization sequence. The golgi localization sequence can be a yeast golgi localization sequence. The invention also includes yeast harboring this isolated nucleic acid molecule and optionally a nucleic acid molecule encoding a fucosyltransferase or a galactosyltransferase, e.g., a fucosyltransferase is selected from:

Homo sapiens fucosyltransferase 1 (galactoside 2-alpha-L-fucosyltransferase, Bombay phenotype included) (FUT1);

Homo sapiens fucosyltransferase 2 (secretor status included) (FUT2);

Homo sapiens fucosyltransferase 3 (galactoside 3(4)-L-fucosyltransferase, Lewis blood group included) (FUT3);

Homo sapiens fucosyltransferase 4 (alpha (1,3) fucosyltransferase, myeloid-specific) (FUT4);

Homo sapiens fucosyltransferase 5 (alpha (1,3) fucosyltransferase) (FUT5);

Homo sapiens fucosyltransferase 6 (alpha (1,3) fucosyltransferase) (FUT6);

Homo sapiens fucosyltransferase 7 (alpha (1,3) fucosyltransferase) (FUT7);

Homo sapiens fucosyltransferase 8 (alpha (1,6) fucosyltransferase) (FUT8);

Homo sapiens fucosyltransferase 9 (alpha (1,3) fucosyltransferase) (FUT9); and

Homo sapiens protein o-fucosyltransferase (POFUT1).

In one embodiment the invention features a nucleic acid molecule (e.g., a recombinant or isolated nucleic acid molecule encoding a fusion protein comprising a yeast golgi localization sequence, e.g., the golgi localization sequence of VRG4, fused to human GDP-fucose transporter or a functional fragment thereof. In other embodiments the invention features protein comprising, consisting of or consisting essentially of a yeast golgi localization sequence, e.g., the golgi localization sequence of VRG4, fused to hum an GDP-fucose transporter or a functional fragment thereof. The protein can be purified and the purified protein can further include a heterologous amino acid sequence, e.g., an amino-terminal or carboxy-terminal sequence. Also featured are purified fragments of the aforementioned protein, e.g., a fragment of at least about 75, 85, 104, 106, 113 150, 200, 250, 300, 350, 400, or 450 amino acids. The protein or fragment thereof can be modified, e.g., processed, truncated, modified (e.g. by glycosylation, phosphorylation, acetylation, myristylation, prenylation, palmitoylation, amidation, addition of glycerophosphatidyl inositol), or any combination of the above.

In another aspect, the invention features a vector, e.g., a vector containing an aforementioned nucleic acid. The vector can further include one or more regulatory elements, e.g., a heterologous promoter or elements required for translation in yeast. The regulatory elements can be operably linked to the fusion protein in order to express the fusion protein. In yet another aspect, the invention features an isolated recombinant cell, e.g., a yeast cell. containing an aforementioned nucleic acid molecule or vector. The nucleic acid sequence can be optionally integrated into the genome.

A "purified protein", as used herein, refers to a protein that has been separated from other proteins, lipids, and nucleic acids with which it is naturally associated. The protein can constitute at least 10, 20, 50 70, 80 or 95% by dry weight of the purified preparation.

An "isolated nucleic acid" is a nucleic acid, the structure of which is not identical to that of any naturally occurring nucleic acid, or to that of any fragment of a naturally occurring genomic nucleic acid spanning more than three separate genes. The term therefore covers, for example: (a) a DNA which is part of a naturally occurring genomic DNA molecule but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones in a DNA library such as a cDNA or genomic DNA library. Isolated nucleic acid molecules according to the present invention further include molecules produced synthetically, as well as any nucleic acids that have been altered chemically and/or that have modified backbones.

Although the phrase "nucleic acid molecule" primarily refers to the physical nucleic acid molecule and the phrase "nucleic acid sequence" refers to the sequence of the nucleotides in the nucleic acid molecule, the two phrases can be used interchangeably.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

A "heterologous promoter", when operably linked to a nucleic acid sequence, refers to a promoter which is not naturally associated with the nucleic acid sequence.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 10A and 10B are a graph and a chart depicting the results of a study of *Campylobacter* colonization in transgenic mice carrying the FUT1 gene with the WAP promoter that directs the expression of H antigens primarily to lactating mammary gland. Pups fed from transgenic mice cleared colonization 5 to 9 days after challenge with *Campylobacter*. Control pups from non-transgenic mice are unable to clear *Campylobacter* colonization. CFU=colony forming units.

DETAILED DESCRIPTION

Figure 1A:
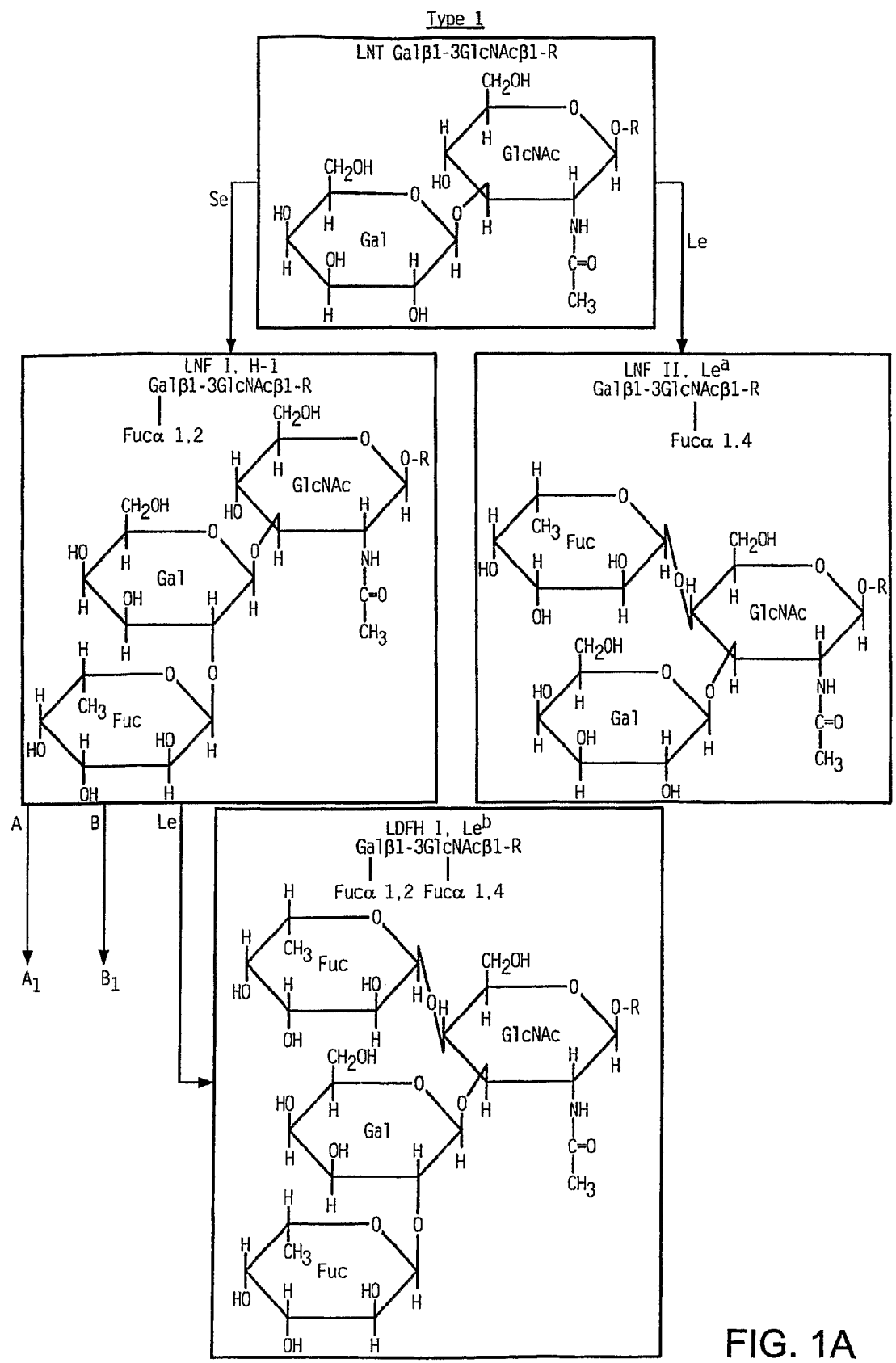
FIG. 1 schematically depicts the Lewis synthesis pathway applied to human milk oligosaccharide structures.

Specific oligosaccharides and specific combinations of oligosaccharides can be used to treat and/or prevent infection by various infectious agents, e.g., infectious agents associated with enteric disorders, respiratory infections, vaginal infections, urinary tract infections, ocular infections, or infections of the oral cavity. Thus, specific combinations of oligosaccharides are expected to be effective in treating and preventing cholera, *Campylobacter* diarrhea, calicivirus diarrhea, *Candida albicans* infection, HIV infection, and other disorders. Oligosaccharides can be administered in monovalent or polyvalent forms, or in combinations thereof. In the monovalent form, free oligosaccharides can be administered singly or in combination. In polyvalent forms two or more oliogosaccharides, which can be the same or different, are attached to a backbone such as a mucin, bile salt stimulated lipase, or bovine serum albumin. The oligosaccharides can be synthesized in vivo by methods described herein. In addition, polyvalent forms of oligosaccharides can be prepared as described herein either partially or entirely in vivo. Also described herein are diagnostic methods for determining which oligosaccharide or combination of oligosaccharides is most likely to be protective for a given individual.

Oligosaccharides

The oligosaccharides that can be used individually or in combination, all of which are depicted below, include: fucosyl oligosaccharides (i.e., Lacto-N-fucopentaose I; Lacto-N-fucopentaose II; 2-Fucosyllactose; 3-Fucosyllactose; Lacto-N-fucopentaose II; Lacto-N-difacohexaose I; and Lactodifucotetraose); non-fucosylated, non-sialylated oligosaccharides (i.e., Lacto-N-tetraose and Lacto-N-neotetraose); sialyl oligosaccharides (i.e., 3'-Sialyl-3-fucosyllactose; Disialomonofucosyllacto-N-neohexaose; Monofucosylmonosialyllacto-N-octaose (sialyl Le$^a$); Sialyl-lacto-N-fucohexaose II; Disialyllacto-N-fucopentaose II; Monofucosyldisialyllacto-N-tetraose); and sialyl fucosyl oligosaccharides (i.e., 3'-Sialyllactose; 3'-Sialyllactosamine; 6'-Sialyllactose; 6'-Sialyllactosamine; Sialyllacto-N-neotetraose c; Monosialyllacto-N-hexaose; Disialyllacto-N-hexaose I; Monosialyllacto-N-neohexaose I; Monosialyl-lacto-N-neohexaose II; Disialyllacto-N-neohexaose; Disialyllacto-N-tetraose; Disialyllacto-N-hexaose II; Sialyl-lacto-N-tetraose a; Disialyllacto-N-hexaose I; and Sialyl-lacto-N-tetraose b). Also useful are variants in which the glucose (Glc at the reducing end is replaced by N-acetylglucosamine (e.g., 2'-fucosyl-N-acetylglucosamine (2'-FLNac) is such a variant to 2'-FL). These oligosaccharides or their non-reducing terminal moieties can be linked to proteins, mucins, lipids, or carbohydrates in various combinations to yield monovalent or polyvalent glycoconjugated molecules. In the case of polyvalent glycoconjugates two or more oligosaccharides are linked to a backbone either directly or via a linker. The two or more oligosaccharides can be the same or different. For example, one or more 2'-FL and one or more 2'-FLNAc can be linked to human serum albumin.

Figure 1B:
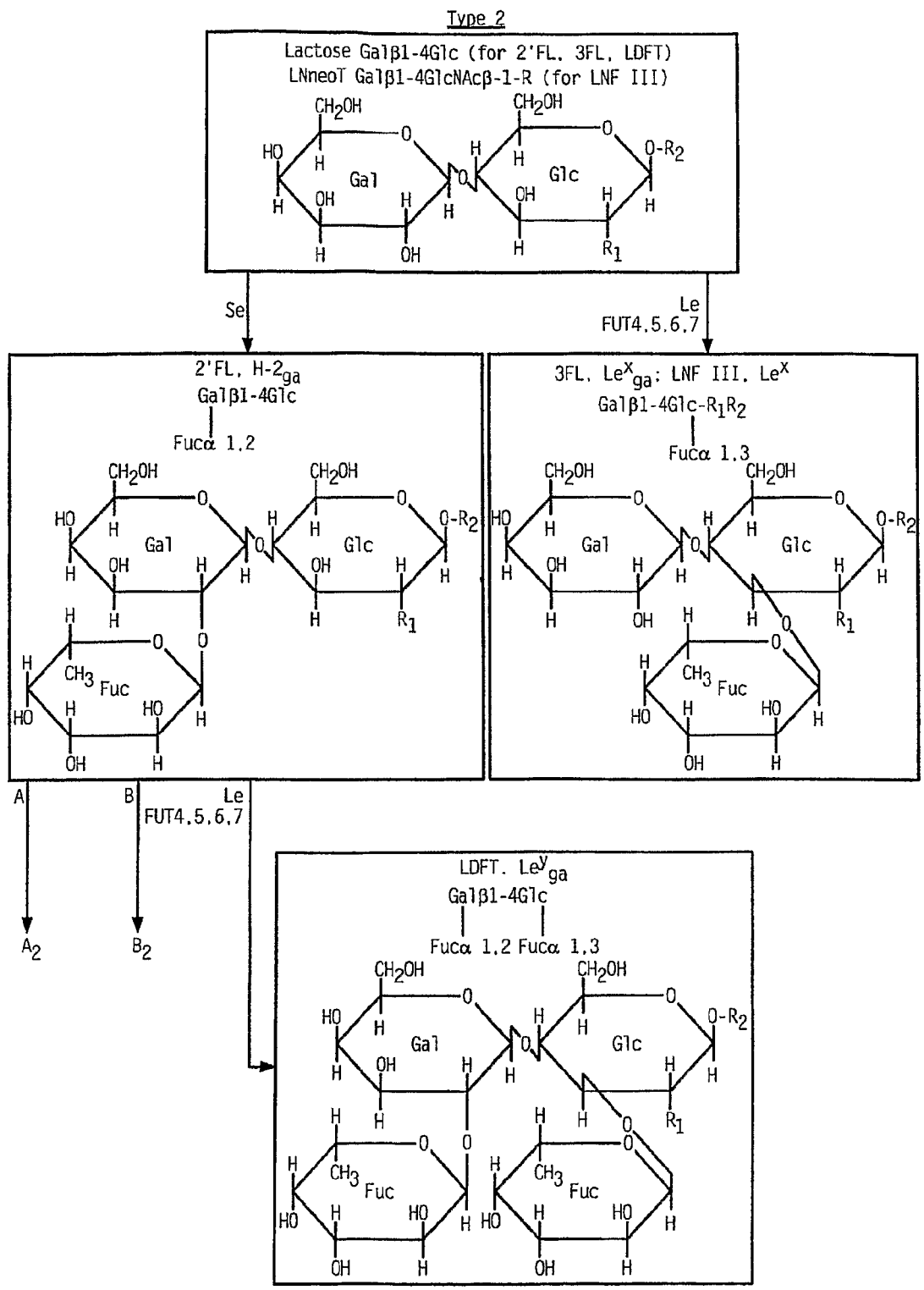

The oligosaccharides noted above are commonly found in human milk. FIG. 1 schematically depicts the Lewis synthesis pathway applied to human milk oligosaccharide structures. The core type 1 structure, lacto-N-tetraose (LNT), is Galβ1, 3GlcNAc on the terminal end of lactose (—R). The core for the most abundant type 2 structures in milk includes lactose (for 2'-FL, 3-FL, and LDFT), lacto-N-neo-tetraose (for LNneoT), and Gal-1,4GlcNAc on a lactose terminus (for LNF-III). Lewis structural moieties are based on a backbone ending in Gal-GlcNAc; however, the most prevalent type 2 structures in human milk contain lactose (Gal-Glc) and therefore are defined as the glucose analogs (ga) to the type 2 Lewis structures, where —$R_1$ is —OH and —$R_2$ is —H. True Lewis structures, such as LNF-III, have an R1 of N-acetyl and an R2 of lactose or lactosamine. Abbreviations for the fucosyltransferase genes are: Se (secretor gene, FUT2), Le (Lewis gene, FUT3), and FUT4,5,6,7,9 (Lewis gene family of 3-fucosyl-transferases). Blood group A and B structures, synthesized from H-1 and H-2 antigens, have been reported but are not major components of milk oligosaccharides.

| Fucosyl oligosaccharides | | |
|---|---|---|
| 2'FL | 2-Fucosyllactose | Fucα1,2Galβ1,4Glc |
| LNF-I | Lacto-N-fucopentaose I | Fucα1,2Galβ1,3GlcNAcβ1,3Galβ1,4Glc |
| LNF-II | Lacto-N-fucopentaose II | Galβ1,3 ↘<br>        GlcNAcβ1,3Galβ1,4Glc<br>Fucα1,4 ↗ |
| 3'FL | 3-Fucosyllactose | Galβ1,4 ↘<br>        Glc<br>Fucα1,3 ↗ |
| LNF-III | Lacto-N-fucopentaose III | Galβ1,4 ↘<br>        GlcNAcβ1,3Galβ1,4Glc<br>Fucα1,3 ↗ |
| LDFH-I | Lacto-N-difucohexaose I | Fucα1,2Galβ1,3 ↘<br>        GlcNAcβ1,3Galβ1,4Glc<br>Fucα1,4 ↗ |
| LDFT | Lactodifucotetraose | Fucα1,2Galβ1,4 ↘<br>        Glc<br>Fucα1,3 ↗ |

| Nonfucosylated, nonsialylated oligosaccharides | | |
|---|---|---|
| LNT | LactoN-tetraose | Galβ1, 3GlcNAcβ1, 3Galβ1, 4Glc |
| LNneoT | LactoN-neotetraose | Galβ1, 4GlcNAcβ1, 3Galβ1, 4Glc |

| Sialyl milk oligosaccharide structures | | |
|---|---|---|
| 3'-SL | 3'-Sialyllactose | NANAα2,3Galβ1,4Glc |
| 3'-SLN | 3'-Sialyllactosamine | NANAα2,3Galβ1,4GlcNAc |
| 6'-SL | 6'-Sialyllactose | NANAα2,6Galβ1,4Glc |
| 6'-SLN | 6'-Sialyllactosamine | NANAα2,6Galβ1,4GlcNAc |
| SLNT-c | Sialyllacto-N-neotetraose c | NANAα2,6Galβ1,4GlcNAcβ1,3Galβ1,4Glc |
| MSLNH | Monosialyllacto-N-hexaose | NANAα2,6Galβ1,4GlcNAc1,6 ↘<br>        Galβ1,4Glc<br>Galβ1,3GlcNAcβ1,3 ↗ |
| DSLNH-I | Disialyllacto-N-hexaose I | NANAα2,3Galβ1,3GlcNAcβ1,3 ↘<br>        Galβ1,4Glc<br>NANAα2,6Galβ1,4GlcNAcβ1,6 ↗ |

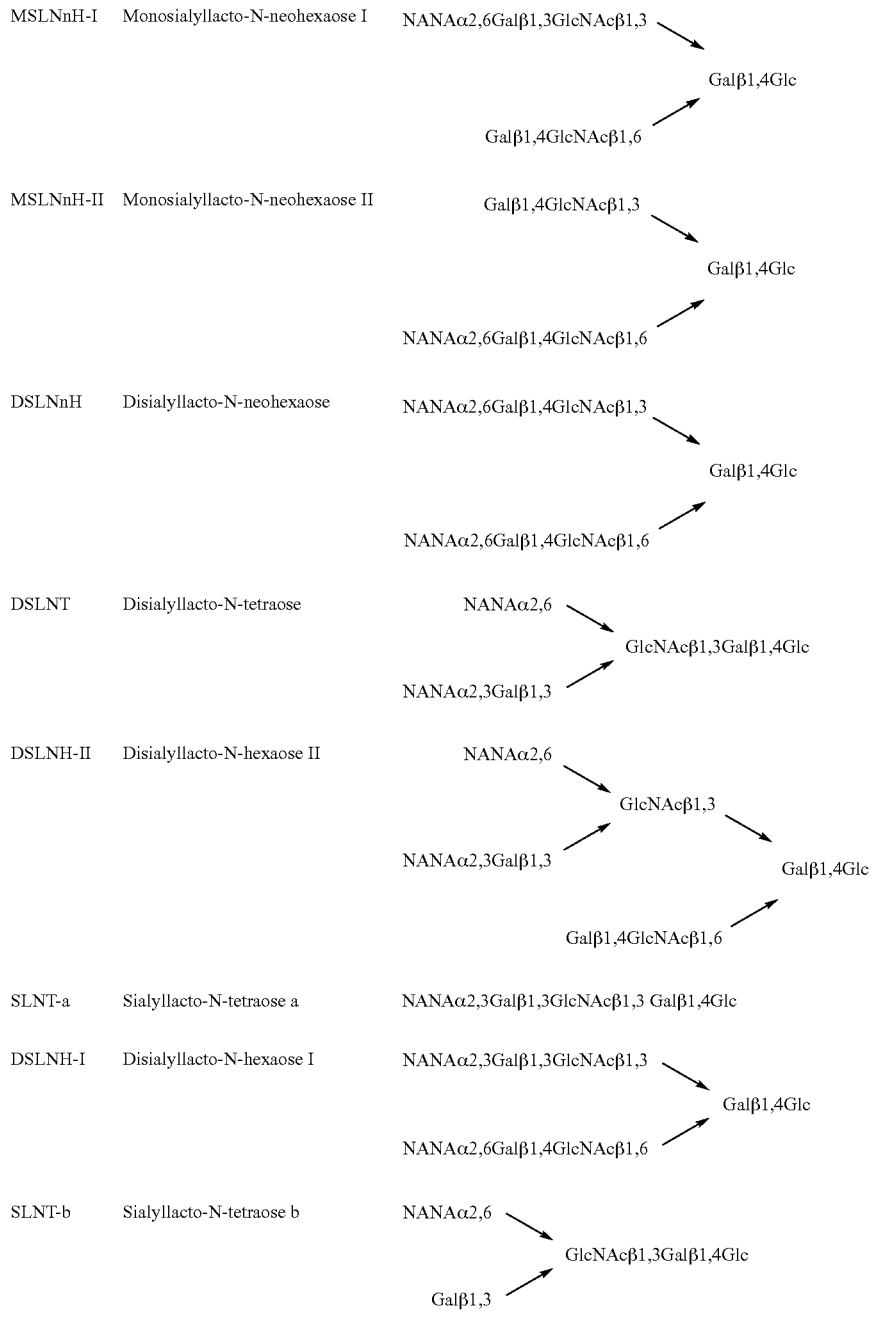
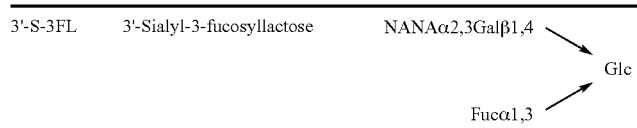

| | -continued | |
|---|---|---|
| | Sialyl fucosyl oligosaccharides | |
| DSFLNH | Disialomonofucosyllacto-N-neohexaose | |
| MFMSLNO | Monofucosylmonosialyllacto-N-octaose (sialyl Le$^a$) | |
| SLNFH-II | Sialyllacto-N-fucohexaose II | |
| DSLNFP-II | Disialyllacto-N-fucopentaose II | |
| MFDLNT | Monofucosyldisialyllacto-N-tetraose | |

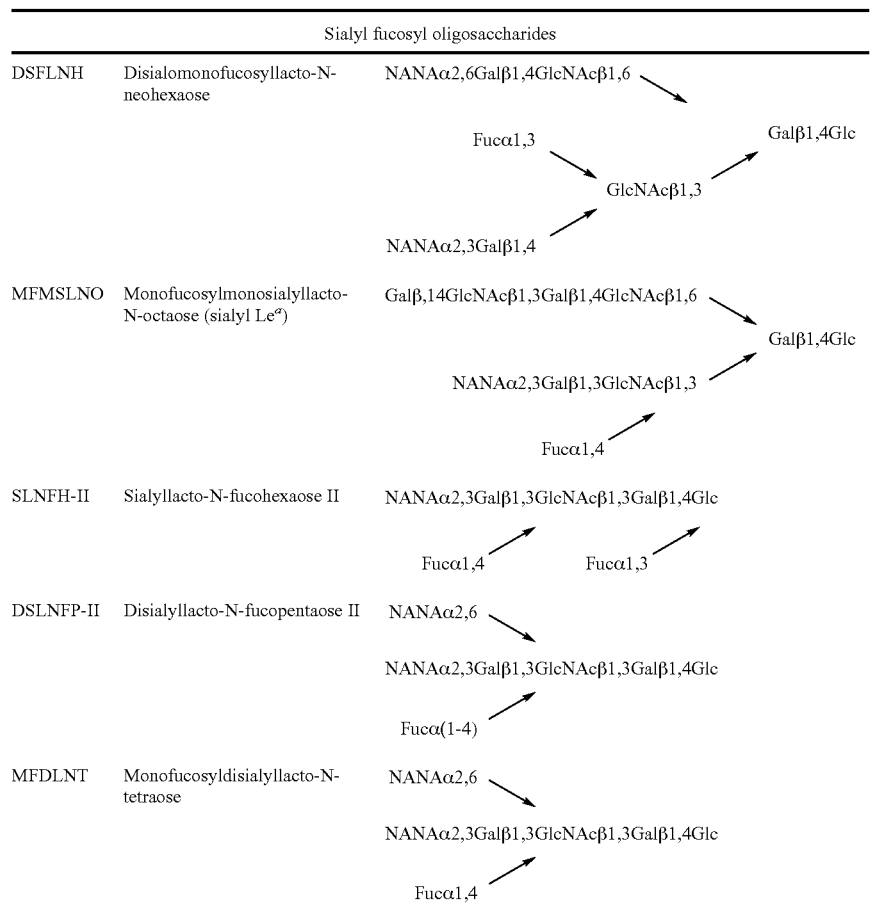

Oligosaccharides for Linking to Proteins

As discussed in greater detail below, the above described milk oligosaccharides can be covalently attached to a protein to create O-linked (to serine or threonine) or N-linked (to asparagines) oligosaccharides. When the milk oligosaccarides are directly linked to a protein the Glc at the reducing end of oligosaccharide must be replaced by GlcNAc to create N-Acetyl glucosamine versions of the oligosaccharides as shown below.

| Fucosyl oligosaccharides for covalent attachment to proteins |
|---|
| 2'FL-N    Fucα1,2Galβ1,4GlcNAc |
| LNF-I-N   Fucα1,2Galβ1,3GlcNAcβ1,3Galβ1,4GlcNAc |

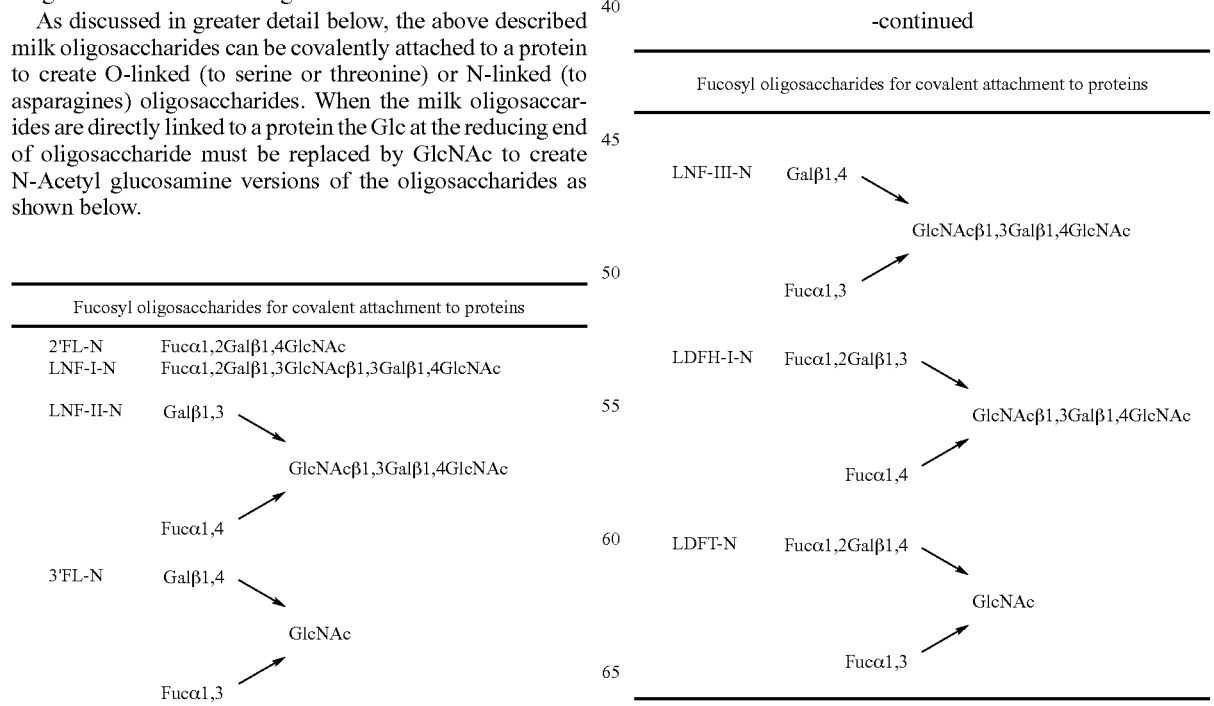

| Non-fucosylated, nonsialylated oligosaccharides for attachment to proteins | |
| --- | --- |
| LNT-N | Galβ1,3GlcNAcβ1,3Galβ1,4GlcNAc |
| LNneoT-N | Galβ1,4GlcNAcβ1,3Galβ1,4GlcNAc |
5
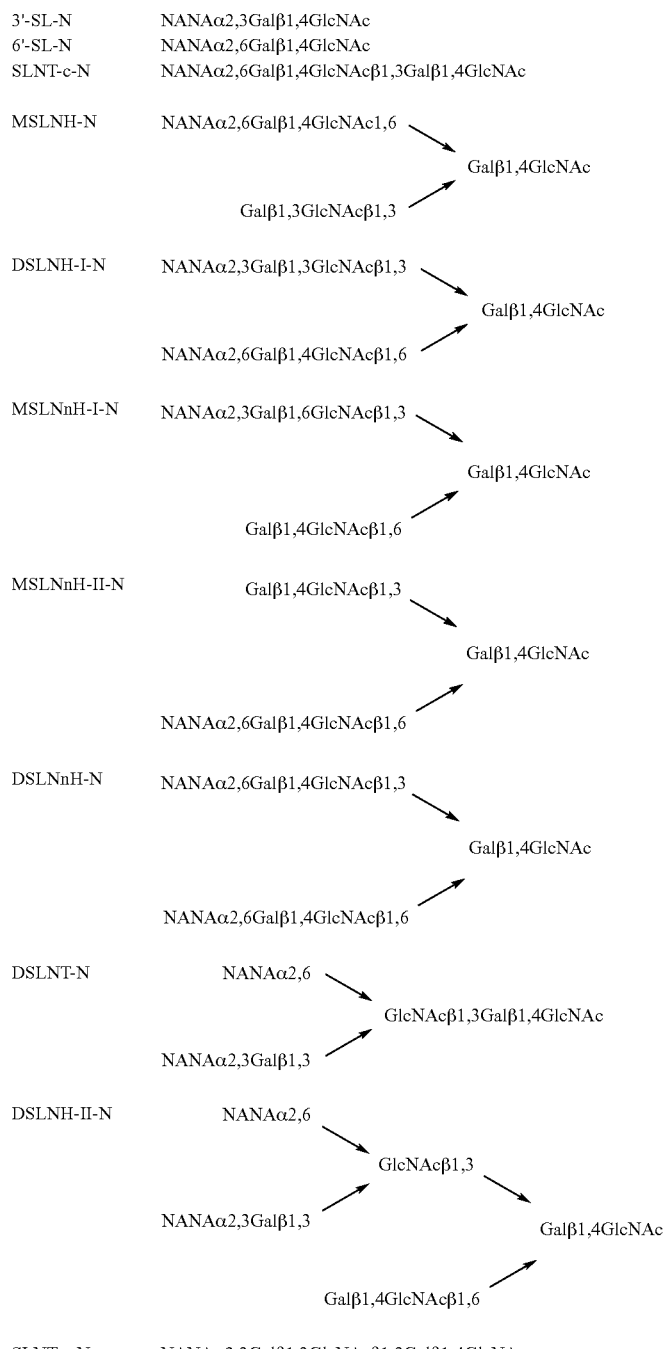

-continued
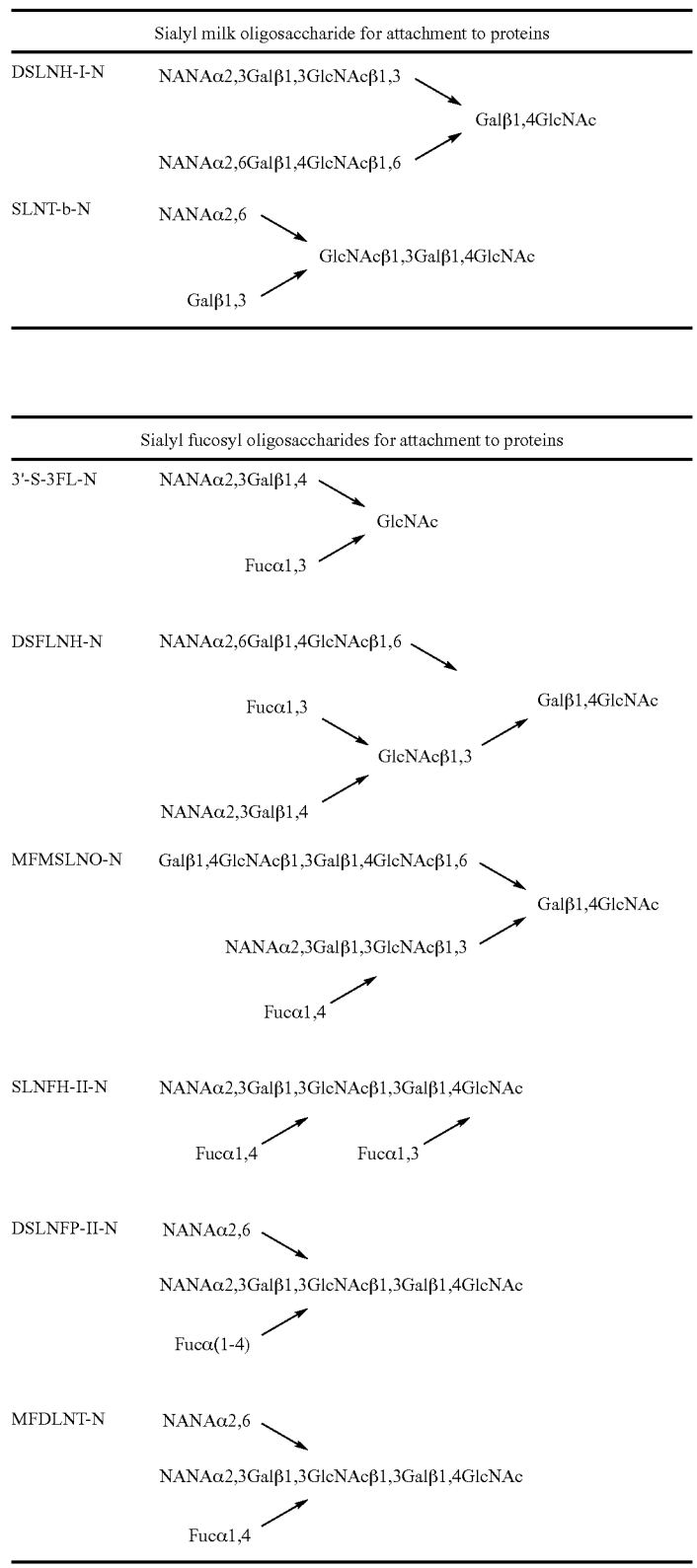
Also useful are variants of LNT, LNneoT, LNT-N, and LNneoT-N having multiple copies (2, 3, 4, 5, 6, 7, 8, 9, 10, 15, 20, 25, 30, 40, 45, or 50 or more) of the internal Gal residue.
Infectious Agents
The compositions and methods described herein can be used to treat and/or prevent infection by a variety of infectious agents that recognize oligosaccharides. The compositions can be used to treat and/or prevent infection by *Campylobacter, V. cholerae*, EPEC, ETEC, EHEC, *Shigella, Listeria, Candida albicans*, HIV, Noroviruses, rotavirus, *Helicobacter pylori*, and other infectious agents of the respiratory tract, alimentary canal, vaginal tract, urinary tract, and eye.

Campylobacter

*Campylobacter* strains are among the most common human and veterinary pathogens worldwide (47-54). Although diarrhea is the most frequent clinical presentation associated with *campylobacter*, a broad clinical spectrum is observed with this infection, including bacteremia, localized infection, and Guillain-Barre Syndrome, a severe immunoreactive complication (47,48). In the United States, the estimated incidence of *campylobacter* is two million symptomatic infections per year, approximately 1% of the U.S. population (49). Population-based studies in England, the U.S., and Sweden have shown a bimodal distribution, with a peak of illness in children less than 5 years of age and a second peak in adolescents and young adults 15 to 29 years old (50-54). The highest isolation rate (15 cases per 100,000) occurs in the first year of life (51). In endemic areas of developing countries, the isolation rate among children with diarrhea is 8% to 45%, with a similar rate of isolation among asymptomatic children (55,56). The annual incidence of *campylobacter* infections can be as high as 2.1 episodes per child-year. Foodborne infections are an emerging concern affecting millions of individuals every year. *Campylobacter* is the second most common cause of foodborne infection after calicivirus (49,50). The alarming increase in multiply antibiotic resistant strains of *campylobacter* being isolated probably results from the use of quinolones in veterinary medicine and as animal food supplements (57).

Children living in endemic areas develop effective natural immunity to *campylobacter* infection as the result of an intense early exposure to the organism (55,56). While immunoglobulins in human milk provide important protection against *campylobacter* as well as other causes of respiratory and gastrointestinal tract infections (58-60), non-immunoglobulin components in human milk also appear to play a dominant role (61-63). Among the non-immunoglobulin protective factors in human milk, the oligosaccharides and glycoconjugates appear to be the most important (30,35,45). It appears that the initial steps of attachment of *campylobacter* to the host cell surface, critical to infection, involve binding to epithelial cell surface glycoconjugates (2,28,64). Human milk oligosaccharides with structural homology to these ligands may inhibit binding by the pathogen (2). Thus, variable expression of these oligosaccharides in milk due to maternal genetic heterogeneity may influence the risk of infection in breastfed infants (42,65,66).

Recent advances in understanding the pathogenesis of *campylobacter* infection have followed the sequencing of its complete genome (67). The ability of *campylobacter* to adhere to and invade the epithelial cells of the ileum and cecum is well known (68-73). Motility and chemotaxis play a major role in the localization of bacteria in the lower part of the intestine (74-78). Studies of the chemotactic behavior of *campylobacter* have shown a positive response to the presence of fucose, but not other sugars, as well amino acids such as aspartate, cysteine, glutamate and serine (76). L-Fucose is an important constituent of both bile and mucin. These may be important factors for the affinity of the organism for the gall bladder and the lower intestinal tract. Environmental and chemotactic stimuli specifically upregulate the *C. jejuni* flaA sigma 28 promoter (77). High pH, osmolarity, and bile salts, including deoxycholate, also upregulate the fla promoter while high viscosity results in downregulation of the fla promoter. Considering that bile and mucin are mixed together in the intestine, and that *C. jejuni* colonization of the mucin layer is a prerequisite for pathogenesis in vivo, the overall response would be an increase in flaA synthesis and chemotaxis towards the mucin layer. These data explain the importance of fucose in the pathogenesis of *campylobacter* infection in the gastrointestinal tract (79).

Early studies demonstrated inhibition of *campylobacter* adherence to intestinal epithelial cells by L-fucose (80). Fucosylated human milk oligosaccharides inhibit cell adherence in vitro and colonization of gut mucosa in vivo by (28). Characterization of these human milk carbohydrate residues showed that α1,2-fucosylated oligosaccharides are the main active components, and that these oligosaccharides, particularly those containing H-2 epitopes, can inhibit *campylobacter* adherence to its host receptor. The specificity of binding to α1,2-fucosyl moieties was confirmed by transfecting Chinese hamster ovary (CHO) cells with the human gene for human α1,2-fucosyltransferase whose expression product catalyzes the final step of H antigen synthesis (81). While parental non-transfected CHO cells (which do not express H antigen) are not infected with invasive *campylobacter*, transfected cells are susceptible to adherence and invasion by *campylobacter*. The differential expression of blood group antigen H-2 at different sites of the gastrointestinal tract could explain the essential features of the pathology of *campylobacter* diarrhea, and likewise, the localization of infection. Mice transfected with the FUT1 gene, flanked by the murine whey acidic protein promoter, specifically express FUT1 in milk during lactation (82). These transfected mice produce large amounts of H-2 antigens in milk, whereas the wild type mice produce none. Pups nursing these transfected dams were protected against intestinal colonization by *campylobacter*. These data support the concept that H antigens are the intestinal ligands essential for the binding of *campylobacter* to the intestinal tract. In milk, soluble ligands containing H-2 epitopes can serve as receptor analogs that protect infants from *campylobacter* infection, and they may represent an important component of the innate immune system of human milk (63).

Cholera

Susceptibility to cholera appears to be related to the ABH (O) tissue-blood group antigens (83, 84). Studies of immunity to experimental cholera in human volunteers showed that blood group O was significantly more frequent in volunteers who developed severe cholera (stool volume >5.0 L). A large epidemiological study done in Bangladesh demonstrated that patients with cholera were twice as likely to have O blood group as community controls (44). This study also showed that individuals with the most severe type of diarrhea were most likely to be of blood group O (68% versus 31%; P<0.01). One possible explanation for the increased severity of cholera in persons of blood group O is that an enhanced adherence of vibrios to the intestinal mucosa may occur in such individuals. Because of this increased susceptibility of individuals of O blood group to develop severe cholera, the immunogenicity and protective efficacy of a cholera vaccine in persons of this group have also been examined. Randomized, double-blind, placebo controlled studies with an attenuated cholera vaccine showed a stronger immune response in persons of the O blood group type, with significantly higher reciprocal geometric mean titers than the non-O group vaccinees (85); this information supports the concept that *Vibrio cholerae* adheres more avidly to intestinal mucosa of persons of blood group O, inducing a heightened vibrocidal response. However, the biological and molecular basis for this genetically related protection has not yet been elucidated. Previous studies have demonstrated that hemagglutination produced by *V. cholerae* with human O erythrocytes can be inhibited with L-fucose (86). The human intestinal epithelium is rich in glycolipids and glycoproteins of the ABH(O) and Lewis histo-blood group antigens (87). The H(O) antigen consists of a backbone of fucose α1,2DGalβ1. It is therefore conceivable that the H antigen serves as a receptor for *V. cholerae*. As we have previously shown in *campylobacter*, *V. cholerae* also binds in vitro to ABH-Lewis neoglycoproteins and also attaches preferentially to α1,2 fucose determinants expressed on the surface of FUT1-transfected CHO cells (69). There is also recent evidence that the B subunit of cholera toxin and the labile toxin (LT) of enterotoxigenic *Escherichia coli* not only binds with high affinity to GM1 ganglioside, but LTB also interacts with N-acetyl lactosamine-terminated glycoconjugates (87,88).

Other Pathogens

An association between Lewis and secretor histo-blood group genotypes appears to be associated with a number of different pathogens. For example, Ikehara and others have reported that Lewis and secretor histo-blood group genotypes are associated with differing risk of infection with *Helicobacter pylori* (42). Huang et al and have reported that secretor blood group individuals have increased susceptibility to several strains of caliciviruses (3). Influenza virus binding has been shown to vary in relation to host Lewis blood group antigens (89). Further, Raza et al reported that secretor children have increased risk of hospitalization for respiratory infections due to influenza viruses A and B, rhinoviruses, respiratory syncytial virus, and echoviruses (90).

Resistance to ST-associated *E. coli* (27, 6), and several strains of caliciviruses is associated with inhibition by α1,2-linked fucosylated oligosaccharide structures. A human milk fucosyl oligosaccharide inhibits the ability of ST to induce diarrehea in vivo. Studies with caliciviruses have shown that Norwalk virus-like particles bind to tissue sections of the gastro-duodenal junction from secretors but not from non-secretors (5), and that binding is blocked by milk from a secretor (91). Volunteers challenged with Norwalk virus become symptomatically infected only if they are secretors. Moreover, it appears that $Le^b$ epitopes and other 2-linked fucosylated oligosaccharide structures inhibit binding by major strains of caliciviruses.

Synthesis of Oligosaccharides and Fucosylated Glycans

Described below are methods, employing recombinant yeast and bacteria, for the synthesis of oligosaccharides and various fucosylated glycans.

Conventionally, oligosaccharides are isolated from milk, e.g., human milk, or chemically synthesized. Oligosaccharides isolated human milk are generally very expensive and may be contaminated with infectious agents. Sophisticated methods for chemically synthesizing oligosaccharides are available. Chemical synthesis of oligosaccharides involves the differential derivatization of the hydroxyl groups of each sugar that is added in sequence to form the desired structure. The hydroxyl group that participates in each linkage must be protected by a different protecting group than the hydroxyl groups that are not involved in linkage. Thus, synthesizing complex structures involves the use of many blocking agents. Over the past 20 years suitable blocking agents have been developed to allow the complete chemical synthesis of complex glycan structures that were heretofore not feasible.

More recently, the cloning of certain biosynthetic genes has made available certain of the components required chemienzymatic synthesis of oligosaccharides. In this approach, genes encoding enzymes that catalyze critical steps in the formation of essential precursors or enzymes that use these precursors to make the desired product are inserted into the appropriate plasmids and transfected into a well-defined bacterium such as *E. coli*. The enzyme is isolated and purified and attached to a solid-phase, which is then packed into a column. The precursors for each reaction are put through the column, and the product is isolated from the eluate. Examples of this technology includes the conversion of the GDP-mannose to GDP-fucose, and the subsequent transfer of the fucose from GDP-fucose onto lactose to form 2'-FL (92). This approach readily allows scale up of the reaction to produce gram- and kilogram quantities of both 2'-FL and 2'-FLNAc.

Production of Oliogosaccharides in Recombinant Yeast

Suitable yeast include those belonging to the genera *Candida* (e.g., *Candida albicans*), *Debaryomyces*, *Hansenula*, *Kluyveromyces*, *Pichia* and *Saccharomyces* (e.g., *Saccharomyces cerevisae* and *Pichia pastoris*). However, other organisms can be used for in vivo production of oligosaccharides, e.g., *E. coli* and baculovirus systems.

In generating the vectors and engineered yeast described below any of a variety of promoters, expression control elements and termination sequences can be employed. Any promoter that is generally used for a yeast expression system and allows expression of a gene in yeast can be used. Examples of such a promoters include PGK, GAP, TPI, GAL1, GAL1O, ADH2, PH05 and CUP1. Useful terminators include ADH1, TDH1, TFF and TRP5.

A nucleic acid sequence introduced into yeast can be integrated into the yeast genome or can be carried on a vector, e.g., a vector containing the yeast 2μ sequence that allows autonomous replication. A number of autonomous vector for expression in yeast are know, including: YEp51, pYES2, YEp351, YEp352 or the like. Often the vectors include a selectable maker such as HIS3, TRP1, LEU2, URA3, ADE2, SUC2, or LYS2.

Vectors and expression systems suitable for expressing proteins in yeast are well known to those of ordinary skill in the art. Such vectors and expression systems are described in U.S. Published Patent Application 20010012630; U.S. Pat. Nos. 6,312,923; 6,306,625; 6,300,065; 6,258,566; 6,172,039; 6,165,738; 6,159,705; 6,114,147; 6,100,042; 6,083,723; 6,027,910; 5,876,951; 5,739,029; 5,602,034; 5,482,835; 5,302,697; and RE 37,343.

Production of 2'-FL and 2'-FLNAc In Vitro

2'-FL and 2'-FLNAc can be produced by: 1) providing a genetically engineered yeast (e.g., *Saccharomyces cerevisiae*) that produces GDP-fucose from GDP-mannose, 2) obtaining a fraction from the yeast that contains GDP-fucose and 3) exposing the fraction to the appropriate fucosyltransferase and substrate to produce, e.g., 2'-FL or 2'-FLNAc.

Yeast which produce GDP-fucose can be created by transforming yeast with: 1) a nucleic acid molecule encoding a GDP-mannose 4, 6 dehydratase (e.g., *H. pylori* GDP-mannose 4, 6 dehydratase; Genbank® Accession No. AAD05625.1 GI:4154547; SEQ ID NO:6 or *E. coli* GMD), an enzyme which converts GDP-mannose to GDP-4-keto-6-D-mannose, and 2) a nucleic acid molecule encoding GDP-4-keto-6-deoxy-alpha-D-mannose 3,5-epimerase-4-reductase (e.g., *H. pylori* GDP-L-fucose synthetase; GenBank® Accession No: AAL33678.1 GI:17017466; SEQ ID NO:7 or *E. coli* GMER(FX)), an enzyme which converts GDP-4-keto-6-D-mannose to GDP-L-fucose via epimerization and reduction. One approach for engineering yeast to produce GDP-mannose has been described previously (93). GDP-fucose can be partially or completely purified from the genetically engineered yeast that have been cultured under conditions which permit the synthesis of GDP-fucose. The fully or partially purified GDP-fucose can be converted to 2'-FL using purified *H. pylori* alpha-1,2-fucosyltransferase (FucT2; GenBank Accession No. AAC99764 GI:4093139; SEQ ID NO:8) with lactose essentially as described previously (92).

In one embodiment, GDP-fucose is produced in yeast expressing *E. coli* GDP-D-mannose-4,6 dehydratase (encoded by the gmd-gene) and *E. coli* GDP-4-keto-6-deoxy-D-mannose epimerase/reductase (encoded by the wcaG-gene). The *E. coli* genes can be transformed into yeast using a vector referred to as the pESC-leu/gmd/wcaG vector. To create this vector, the *E. coli* gmd-gene and wcaG-gene, i.e., GMER (FX) is inserted into pESC-leu-vector under GAL1 and GAL10 promoters, respectively. The gmd gene was inserted in frame with c-myc-epitope and the wcaG gene was inserted in frame with the FLAG-epitope. *S. cerevisiae* transfected with this vector can produce approximately 0.2 mg/L of GDP-fucose without addition of any external GDP-mannose (93). As explained above, the synthesis of 2'-FL and 2'-FLNAc can be carried out using fucosyltransferase enzymes expressed in *E. coli*, e.g., human (FUT1 and FUT2) or *H. pylori* (FucT2). These fucosyltransferase genes are inserted into *E. coli* an appropriate vector such as pGEX4T-1, and overexpressed. The fusion protein is purified by affinity chromatography on a GSTrap-column (Pharmacia/Amersham Biosciences). The purified protein can be covalently linked to sepharose through the solid phase reductive amidation. GDP-fucose and lactose in a suitable buffer (e.g., PBS) is passed over the column to produce 2'-FL. GDP-fucose and N-acetylactosamine are passed over the column to produce 2'-FLNAc. Excess GDP-fucose and nucleotide phosphate are be removed by ion exchange. The fucosylated oligosaccharides are separated from their starting materials by passing them through a *Ulex europaeus* affinity column. The yield and purity of these products is assessed by HPLC analysis of the resulting oligosaccharides.

Production of 2'-FL and 2'-FLNAc In Vivo Using Cell Wall Expressed Transferases

Described below is an improved method for synthesis of oligosaccharides. The method entails the use of yeast that have been genetically engineered to: 1) convert GDP-mannose to GDP-fucose; 2) contain a fucosyltransferase so that they can produce 2'-FL or another fucosylated products of interest in vivo.

For coversion of GDP-mannose to GDP-fucose in yeast, the cells are engineered to express a suitable GDP-mannose 4,6 dehydratase gene. For example, *H. pylori* GDP-mannose 4,6 dehydratase (Genbank Accession No. AAD05625.1 GI:4154547; SEQ ID NO:6). This enzyme converts GDP-mannose to GDP-4-keto-6-D-mannose. The yeast is also engineered to express a suitable GDP-4-keto-6-deoxy-alpha-D-mannose 3,5-epimerase-4-reductase (e.g., *H. pylori* GDP-L-fucose synthetase; GenBank® Accession No: AAL33678.1 GI:17017466; SEQ ID NO:7), which converts GDP-4-keto-6-D-mannose to GDP-L-fucose via epimerization and reduction.

In this method fucosyltransferase is expressed on the extracellular side of the yeast cell wall in order to effectively produce fucosylated glycans. This is accomplished by creating a fusion protein in which all or a functional portion of the yeast cell wall protein, PIR, is fused to the amino terminus of a fucosyltransferase such as *H. pylori* FucT2 or human α-1,3,fucosyltransferase (FucT; encoded by the FUT6 gene). The generation of nucleic acid molecules encoding such proteins is described in Abe et al. (FEMS Yeast Research 4:417, 2004) and Abe et al. U.S. Published Application 20030059872.

Useful PIR include *S. cerevisiase* PIR1 (SEQ ID NO:1; GenBank® Accession No. Q03178 GI:417492). In this 341 amino acid (aa) protein, aa 1-18 is the signal sequence, aa 19-63 is the propeptide, 61-341 is the mature protein, within which aa 83-101, 102-125, 126-144, 145-163, 164-182, 183-201 and 202-220 are repetitive regions. *S. cerevisiase* PIR2 (SEQ ID NO:2; GenBank® Accession No. BAA02886.1 GI:218459); and PIR3 (SEQ ID NO:3; GenBank® Accession No. S37788 GI:481107).

Fucosyltransferases which can be fused include human galactoside 2-alpha-L-fucosyltransferase 2 (fucosyltransferase 2; FUT2; GenBank® Accession No. Q10981; GI:1730125; SEQ ID NO:4). This 343 aa protein has a transmembrane domain that extends from aa 15 to aa 28. Since transmembrane domain and sequences amino terminal to the transmembrane domain are not required in the PIR-FUT2 fusion protein, the PIR-FUT2 fusion protein can include aa 29-343 of SEQ ID NO:4 and need not include aa 1-28 of SEQ ID NO:4. Other useful fucosyltransferases include human alpha-(1,3)-fucosyltransferase (galactoside 3-L-fucosyltransferase; fucosyltransferase 6; FUT6; GenBank® Accession No. P51993 GI:1730136; SEQ ID NO:5). This 359 aa protein has transmembrane domain that extends from aa 15 to aa 34. Since transmembrane domain and sequences amino terminal to the transmembrane domain are not required in the PIR-FUT6 fusion protein, the PIR-FUT6 fusion protein can include aa 35-359 of SEQ ID NO:5 and need not include aa 1-34 of SEQ ID NO:5. Fucosyltransferases from other species, such *Helicobacter pylori* as alpha-(1,3)-fucosyltransferase (GenBank® Accession No. AAB93985.1 GI:2240202; SEQ ID NO:6) can be used.

A number of glycosyltransferases, including fucosyltransferases, galactosyltransferases, glucosyltransferases, mannosyltransferases, galactosaminyltransferases, sialyltransferases and N-acetylglucosaminyltransferases are known and can be used in the above-described method. The sequence and activity of glycosyltransferases are described in, for example, U.S. Pat. Nos. 6,291,219; 6,270,987; 6,238,894; 6,204,431; 6,143,868; 6,087,143; 6,054,309; 6,027,928; 6,025,174; 6,025,173; 5,955,282; 5,945,322; 5,922,540; 5,892,070; 5,876,714; 5,874,261; 5,871,983; 5,861,293; 5,859,334; 5,858,752; 5,856,159; 5,545,553; and RE 37,206. Additional transferases are noted below.

Production of Glycans in Yeast Using a GDP-Fucose/Fucosee Antiporter

Described below is a method for producing fucosylated glycans in yeast. This general approach can be used to produce other glycans in yeast. As noted above, yeast, a common food ingredient, is a rich natural source of GDP-mannose that with the addition of the genes for two enzymes will produce GDP-fucoses, which is the direct precursor for the synthesis of fucosylated oligosaccharides and fucosylated glycans. With insertion of fucosyltransferase genes, fucosylated glycans can be synthesized.

The method of the invention improves the production of GDP-fucose and fucosylated glycan by placing all of the all needed genes in one cassette and the providing an antiporter for GDP-fucose/GMP (160). This antiporter shuttles GDP-fucose from the cytoplasm, its site of synthesis, to the lumen of the Golgi, the site of fucosylation (driving the synthesis of more GDP-fucose in the cytoplasm), while shuttling GMP from the lumen of the Golgi (driving fucosylation) to the cytoplasm, where it would be recycled into more GDP-fucose (161).

Production of 2'-fucosyllactose (2'-FL) in Yeast

Both *Saccharomyces cerevisiae* and *Pichia pastoris* can be used to produce fucosylated glycans. First, a single cassette is used to introduce the two enzymes (GDP-mannose 4,6 dehydratase, and GDP-L-fucose synthetase from, for example, *H. pylori*: 162) necessary to produce GDP-L-fucose in situ. A suitable cassette can be produced as follows. First, a plasmid is constructed by replacing the smaller EcoR I/Xba I fragment in pPIC9K with the smaller EcoR I/Xba I fragment from pAO815. The integrative plasmid pPIC9K contains the bacterial kanamycin-resistance gene between HIS4 (the histidinol dehydrogenase gene) and 3' AOX1 (the alcohol oxidase gene) for screening the multi-copy gene transformants. The coding sequences for GDP-D-mannose 4,6-dehydratase (GMD) and GDP-L-fucose synthetase (GFS) are amplified from plasmid DNA pET15b-GMD and pET15b-GFS by PCR using primers incorporating 5' EcoR I sites, and subcloned into the EcoR I site of pPIC9K to generate the plasmids pPIC9K/GMD and pPIC9K/GFS respectively. The GFS expression cassette is removed from pPIC9/GFS with Bgl II/BamH I and subcloned into the BamH I site of pPIC9K/GMD to generate the co-expression vector, which contains expression cassettes for GMD and GFS (163). The genes, now incorporated onto one plasmid, are integrated into the *P. pastoris* chromosome by electroporation with the co-expression plasmid digested with the restriction endonuclease Sal I; transformants are isolated on kanamicin medium. Each gene has its own methanol-inducible alcohol oxidase 1 promoter and transcription terminator on the chromosomal DNA of *P. pastoris* strain GS115 his4. The proteins are co-expressed intracellularly under methanol induction. The fermentation process consists of the three distinctive phases; glycerol batch phase for initial cell growth, glycerol fed-batch phase for AOX1 derepression and high cell density, and induction phase for expression of these enzymes (163) The production of sugar nucleotides is monitored by capillary electrophoresis (164, 165).

The recombinant *S. cerevisiae* for production of GDP-fucose is constructed through mating. First individual expression vectors are created using the plasmid pGLD, which contains the glyceraldehyde-3-phosphate dehydrogenase (GLDp) promoter and phosphoglycerol kinase (PGKt) terminator. Fragments of GMD and GFS genes are inserted into the plasmids.[54] These plasmids are inserted by electroporation into *S. cerevisiae* ATCC60729 (Matα; his, trp1, leu2, ura3) and ATCC60729 (Mata; his, trp1, leu2, ura3). The two kinds of mating types in yeast cells, a-type and α-type, can make a diploid, which carries genes originating from a-type and α-type. Diploids containing GMD and GFS genes are formed and produce the enzymes.

The fermentation process consists of the two phases: 1) batch phase for initial cell growth and expression of these enzymes and 2) fed-batch phase for high cell density and high expression of these enzymes. In the fed-batch phase, the feed medium (200 ml of 80% sucrose solution) is fed using a DO-stat of 50% air saturation. Yeast constructs grown under these conditions are assessed for enzyme expression, stability of plasmids, and overall yield. The production of sugar nucleotides is monitored by capillary electrophoresis (164, 165).

The high capacity for production of GDP-mannose in yeast provides potential capacity for the transformants to produce large amount of GDP-fucose. GDP-mannose production could be further channeled toward GDP-fucose by inhibiting the production of high-mannose structures in the yeast (166, 167). This can be achieved, for example, by using Och1p (alfa 1,6 manosyltransferase) deletion mutants or by including of heterologous genes coding for an alpha 1,2 manosidase, a GlcNac transferase, and a UDP-GlcNac transporter. (Hamilton et al. 2003 Science 301:1244)

Conversion of GDP-mannose to GDP-fucose can be inhibited by moderate build up of GDP-fucose (168, 169). In mammals, this is overcome by an antiporter, a Golgi membrane spanning transporter that shuttles GDP-fucose from the cytoplasm to the lumen of the smooth ER/Golgi, where it is utilized for fucosylation, releasing free GDP, which is returned by the antiporter to the cytoplasm (161). Thus, in cytoplasm, GDP-fucose can be produced as fast as it is consumed. This elegant control mechanism allows extensive fucosylation in mammals, especially in human mammary epithelial cells, which can be introduced into yeast by inserting the antiporter gene responsible for GDP-fucose movement across ER/Golgi membranes (160). For this antiporter to be useful, it must insert itself into the membrane of the Golgi. GDP-mannose, the principal nucleotide sugar for glycosylation in the Golgi of *Saccharomyces cerevisiae*, is transported into the lumen by the antiporter VRG4 gene product (GenBank® Accession No. P40107 GI:729611; SEQ ID NO:9). Mutant Vrg4 proteins lacking the N-terminal cytosolic tail do not localize to the Golgi membrane, while fusion of the N terminus of Vrg4p to non-Golgi membrane proteins promotes their transport to the Golgi; thus, the N terminus navigates protein expression specifically to the Golgi (170). By fusing the N terminus of the Vrg4p yeast antiporter (amino acids 1-53 or 21-53 or 31-53) to the human GDP-fucose transporter (GenBank® Accession No. AAK50397.1 GI:13940506; SEQ ID NO:10; AAK51705.1 GI:14009667; SEQ ID NO:1), it can be directed into the yeast Golgi membrane (171).

Any suitable fucose transporter can be fused to a golgi localization sequence in order to create a fucose transporter that will shuttle fucose to the lumen of smooth ER and golgi. The following GDP-fucose transporters may be used.

1: Genbank® Accession No. Q968A5; gi|20138279|

2: Genbank® Accession No. XP_508388; gi|55635789|

3: Genbank® Accession No. Q9VHT4; gi|20138437|

4: Genbank® Accession No. NP_997597; gi|46877098|

5: Genbank® Accession No. NP_665831; gi|22003876|

6: Genbank® Accession No. EAL38393; gi|54659831|

7: Genbank® Accession No. EAL38067; gi|54659493|

8: Genbank® Accession No. NP_060859; gi|37059731|

9: Genbank® Accession No. AAS46733; gi|44151600|

10: Genbank® Accession No. XP_421127; gi|50748147|

11: Genbank® Accession No. NP_732412; gi|24648166|

12: Genbank® Accession No. NP_723268; gi|24582476|

13: Genbank® Accession No. NP_476859; gi|24639454|

14: Genbank® Accession No. NP_525033; gi|18079265|

15: Genbank® Accession No. NP_524191; gi|17737703|

16: Genbank® Accession No. NP_523502; gi|17648113|

17: Genbank® Accession No. NP_477264; gi|17137388|

18: Genbank® Accession No. BAC40223; gi|26353186|

19: Genbank® Accession No. BAC38127; gi|26348975|

20: Genbank® Accession No. BAC34181; gi|26341038|

21: Genbank® Accession No. BAC32554; gi|26337737|

22: Genbank® Accession No. BAC30770; gi|26334105|

23: Genbank® Accession No. BAC30595; gi|26333755|

24: Genbank® Accession No. BAC28226; gi|26328975|

25: Genbank® Accession No. BAC27199; gi|26326911|

26: Genbank® Accession No. Q96A29; gi|20138280|

27: Genbank® Accession No. NP_200520; gi|15242035|

28: Genbank® Accession No. NP_566487; gi|18400381|

29: Genbank® Accession No. AAO50954; gi|28828290|

30: Genbank® Accession No. NP_502550; gi|25150865|

31: Genbank® Accession No. NP_505467; gi|25150188|

32: Genbank® Accession No. NP_741360; gi|25148765|

33: Genbank® Accession No. NP_503604; gi|25146317|

34: Genbank® Accession No. NP_500371; gi|17538248|

35: Genbank® Accession No. XP_230292; gi|34856560|

36: Genbank® Accession No. AAL62491; gi|18252816|

37: Genbank® Accession No. AAK51705; gi|14009667|

38: Genbank® Accession No. AAK50397; gi|13940506|

39: Genbank® Accession No. AAK50396; gi|13940504|

40: Genbank® Accession No. AAK49910; gi|13936720|

41: Genbank® Accession No. AAK49909; gi|13936718|

42: Genbank® Accession No. AAK49908; gi|13936716|

There are a number of sources of suitable golgi localization sequences, including:

The golgi localization sequence from the *S. cerevisae* GDP-Gal porter (GenBank Accession No. AAT92855.1 GI:51013123) can also be used.

Figure 4:
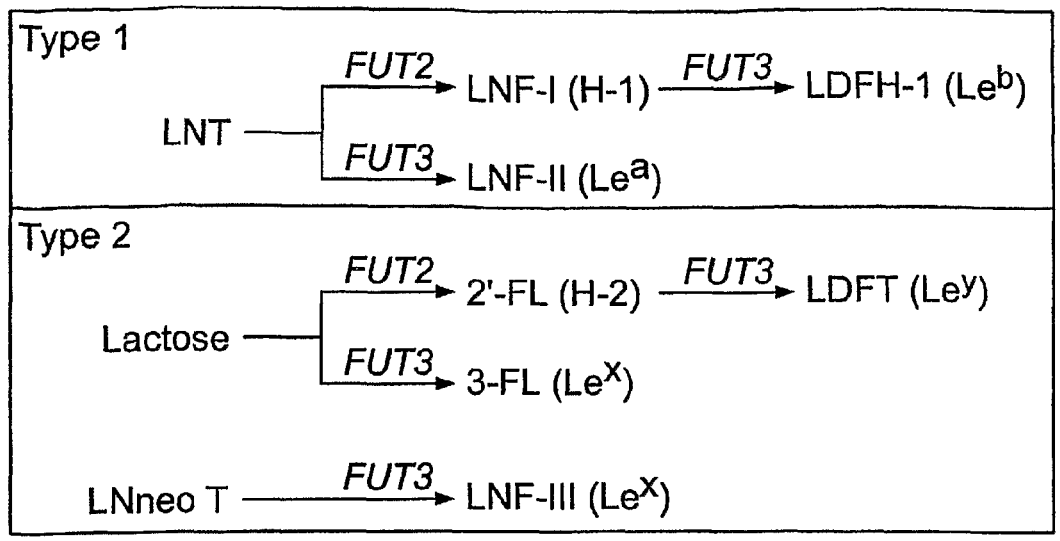
FIG. 4 depicts a synthetic scheme for milk oligosaccharides.
Figure 5:
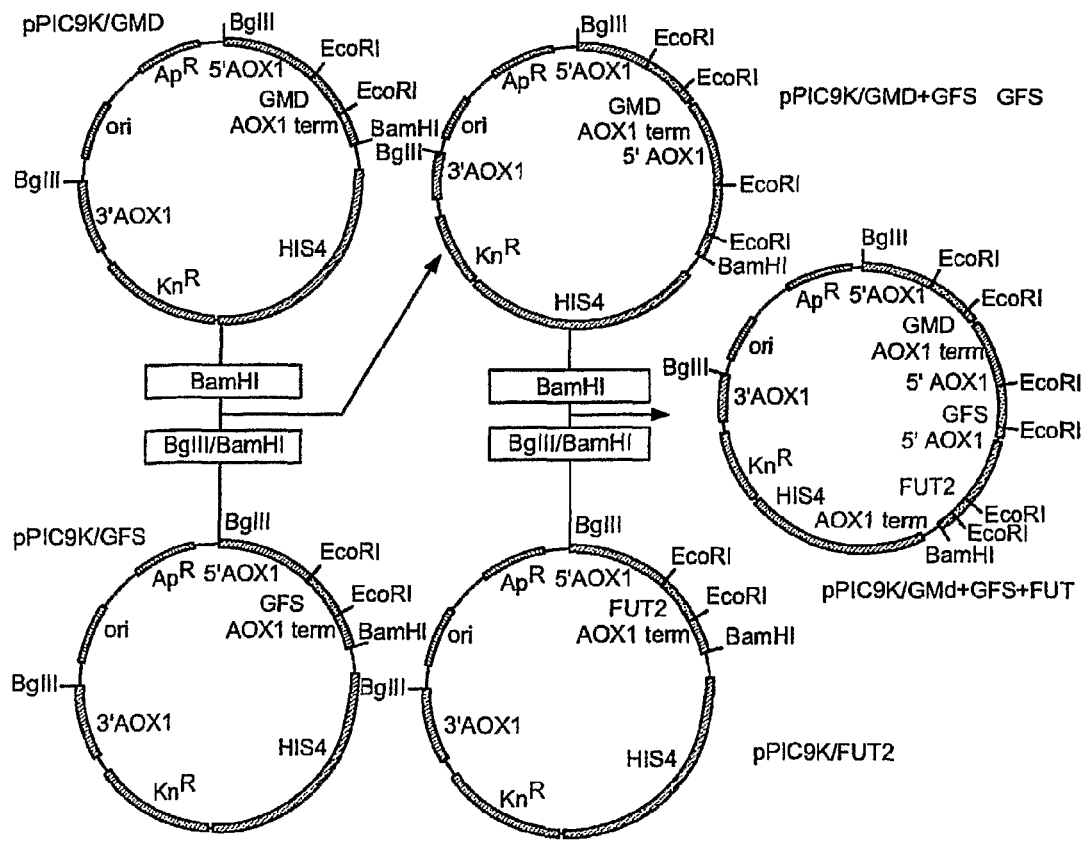
FIG. 5 schematically depicts the construction of a vector useful for producing oligosaccharides in yeast

Yeast Producing 2'-FL, 3-fucosyllactose (3-FL), lactodifucotetraose (LDFT), lacto-N-fucopentaose I, lacto-N-fucopentaose II, or lacto-N-hexaose Many useful oligosaccharides contain lactose at the reducing end and fucose at the nonreducing end. Oligosaccharides of type 1 structure may have fucosyl α1,4 linked to N-acetylglucosamine, whereas those of type 2 structure may have fucosyl α1,3 linked to N-acetylglucosamine or glucose. Either type may contain fucosyl α1,2 linked to galactose. The addition of fucose to an oligosaccharide by a α1,2 linkage is catalyzed by fucosyltransferases produced by FUT2. The addition of fucose by an α1,3 or α1,4 linkage is catalyzed by fucosyltransferases produced by FUT3 or other genes of this family. The synthesis of milk oligosaccharides by pathways defined by these enzymes is described in FIG. 4. Thus, in addition to the two enzyme genes GMD and GFS, the development of yeasts as biocatalysts for synthesis of human milk oligosaccharides requires the co-production of FUT2, FUT3, or both, in addition to a GDP-fucose anti-porter expressed on the golgi. Plasmid construction of FUT2 and FUT3, and the transformation of yeast (*P. pastoris* and in *S. cerevisiae*) is performed as discussed above. For example, the insertion of the FUT2 (or FUT3, or both) genes into *P. pastoris* can be accomplished by transformation with a vector constructed as shown in FIG. 5. When the recombinant yeasts are fed lactose, they will produce 2'-FL, 3-fucosyllactose (3-FL), or lactodifucotetraose (LDFT). When the yeasts are fed lacto-N-tetraose, they will produce the type 1 Lewis epitopes, lacto-N-fucopentaose I, lacto-N-fucopentaose II, or lacto-N-hexaose.

Fucosyltransferases and Galactosyltransferases

Various desired oligosaccharides can be produced by expressing the proper transferase in the cell. Suitable fucosyltransferases include:

Genbank® Accession No. NM_000148

*Homo sapiens* fucosyltransferase 1 (galactoside 2-alpha-L-fucosyltransferase, Bombay phenotype included) (FUT1)
Genbank® Accession No. NM_000511

*Homo sapiens* fucosyltransferase 2 (secretor status included) (FUT2)
Genbank® Accession No. NM_000149

*Homo sapiens* fucosyltransferase 3 (galactoside 3(4)-L-fucosyltransferase, Lewis blood group included) (FUT3)
Genbank® Accession No. NM_002033

*Homo sapiens* fucosyltransferase 4 (alpha (1,3) fucosyltransferase, myeloid-specific) (FUT4)
Genbank® Accession No. NM_002034

*Homo sapiens* fucosyltransferase 5 (alpha (1,3) fucosyltransferase) (FUT5)
Genbank® Accession No. XM_012800

*Homo sapiens* fucosyltransferase 6 (alpha (1,3) fucosyltransferase) (FUT6)
Genbank® Accession No. XM_056659

*Homo sapiens* fucosyltransferase 7 (alpha (1,3) fucosyltransferase) (FUT7)
Genbank® Accession No. NM_004480

*Homo sapiens* fucosyltransferase 8 (alpha (1,6) fucosyltransferase) (FUT8)
Genbank® Accession No. NM_006581

*Homo sapiens* fucosyltransferase 9 (alpha (1,3) fucosyltransferase) (FUT9)
Genbank® Accession No. AF375884

*Homo sapiens* protein o-fucosyltransferase (POFUT1)
Suitable Galβ1,3 transferase galactosyltransferases include: β1,3Gal T core (Genbank Accession No.® AF155582); β1,3GalT1 (Genbank Accession No.® AF117222); β1,3GalT2 (Genbank Accession No.® AF288390); β1,3GalT3 (Genbank Accession No.® AF132731); β1,3GalT4 (Genbank Accession No.® AB026730); β1,3GalT5 (Genbank Accession No.® AF145784); and β1,3GalT6 (Genbank Accession No.® AY050570).

Suitable Galβ1,4 transferase galactosyltransferases include: β1,4GalT1 (Genbank Accession No.® D29805); β1,4GalT2 (Genbank Accession No.® AB024434); β1,4GalT3 (Genbank Accession No.® AB024435); β1,4GaltT4 (Genbank Accession No.® AF022367 Lc2 synthase); β1,4GalT5 (Genbank Accession No.® AB004550); β1,4GalT6 (Genbank Accession No.® AB024742); and β1,4GalT7 (Genbank Accession No.® AB028600).

A suitable blood group B Galα1,3 transferase galactosyltransferase is Blood group B Galα1,3 T (Genbank Accession No.® AF134414).

Generally, human FUT1 and FUT2 are useful for adding α1,2 linkages; human FUT3 is useful for adding α1,4 linkages; human FUT5, FUT6, FUT7, and FUT9 are useful for adding α1,3 linkages; and FUT8 is useful for adding α1,6 linkages.

Yeast Producing lacto-N-tetraose (LNT) and lacto-N-neotetraose (LNneoT)

The human milk oligosaccharides include two tetraoses, LNT (Galβ1,3 GlcNAcβ1,3Gal β1,4 Glc) and LNneoT (Galβ1,4 GlcNAcβ1,3 Galβ1,4Glc) that are precursors to common milk fucosyloligosaccharides. To synthesize lacto-N-tetraose, β1,3GlcNAc transferase transfers GlcNAc from UDP-GlcNAc to lactose to synthesize lacto-N-triose II; then galactose is transferred to lacto-N-triose II by GlcNAcβ1,3 Gal transferase. If the genes for this synthesis are inserted into wild-type yeast, LNT will be produced; if inserted into a FUT2 construct, LNF-I will result; if inserted into a FUT3 construct, LNF-II will result; if inserted into a FUT2/FUT3 construct, lacto-N-difucohexaose (LDFH-I) would be the product. Similarly, LNneoT will be synthesized in yeast that has been transformed with a Galβ1,4GlcNAc transferase and GlcNAcβ1,4Gal transferase. These yeasts, when fed lactose, will produce LNneoT. If these genes are inserted into a FUT3 construct, LNF-III would be produced. These transformants arise through integration of the plasmid into the chromosome. The level of geneticin resistance indicates the relative copy number of the integrated plasmid, since resistance is conferred by the kanamycin marker on the plasmid. Generally, high-copy-number integrants are preferred for obtaining a high level of heterologous protein production.

Chemical Synthesis

As an alternative, chemical synthesis methods can be used to prepare oligopeptides that are useful in the various methods and compositions described herein.

Figure 2:
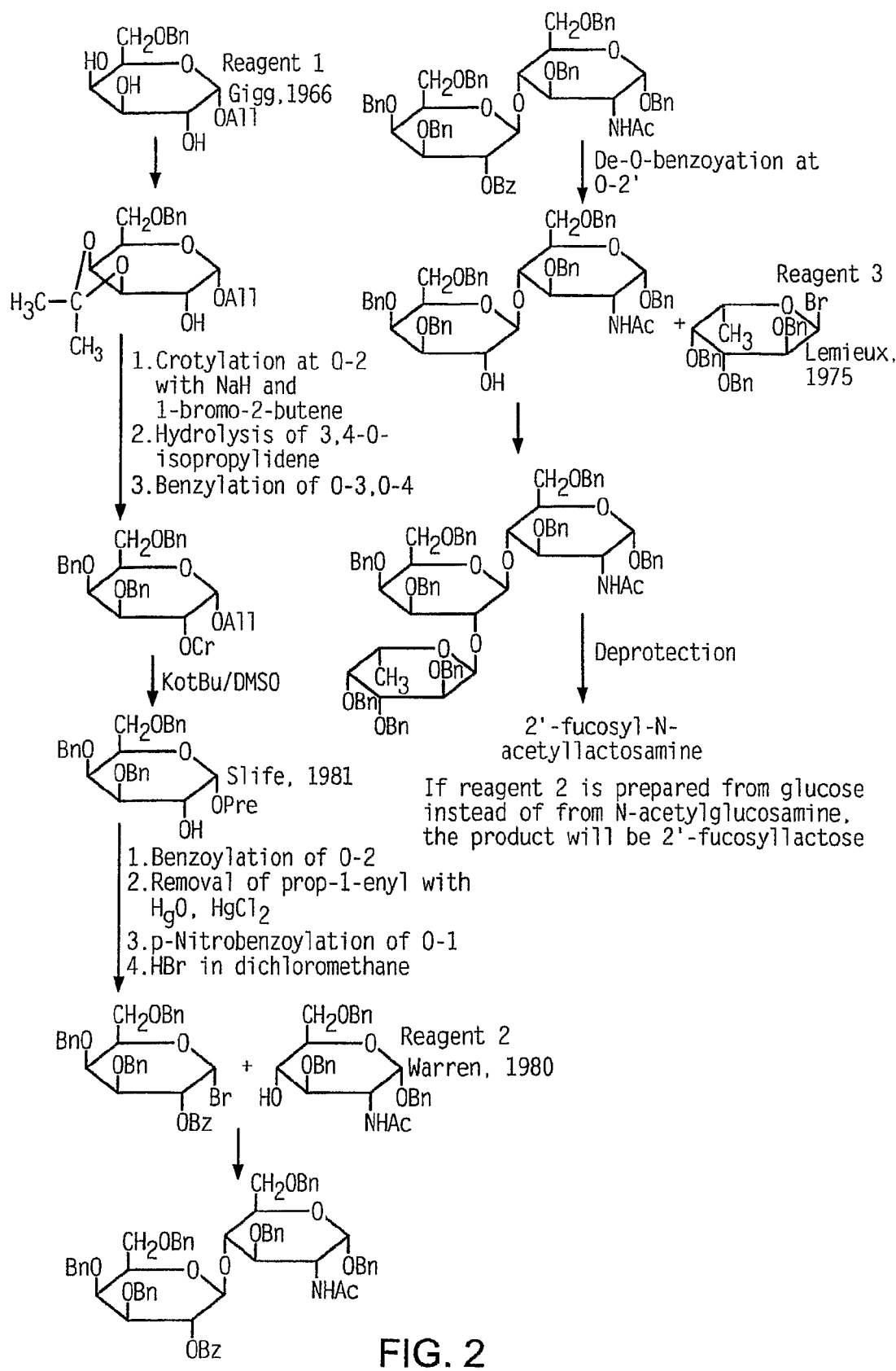
FIG. 2 schematically depicts a method for chemically synthesizing certain oligosaccharides.
Figure 3:
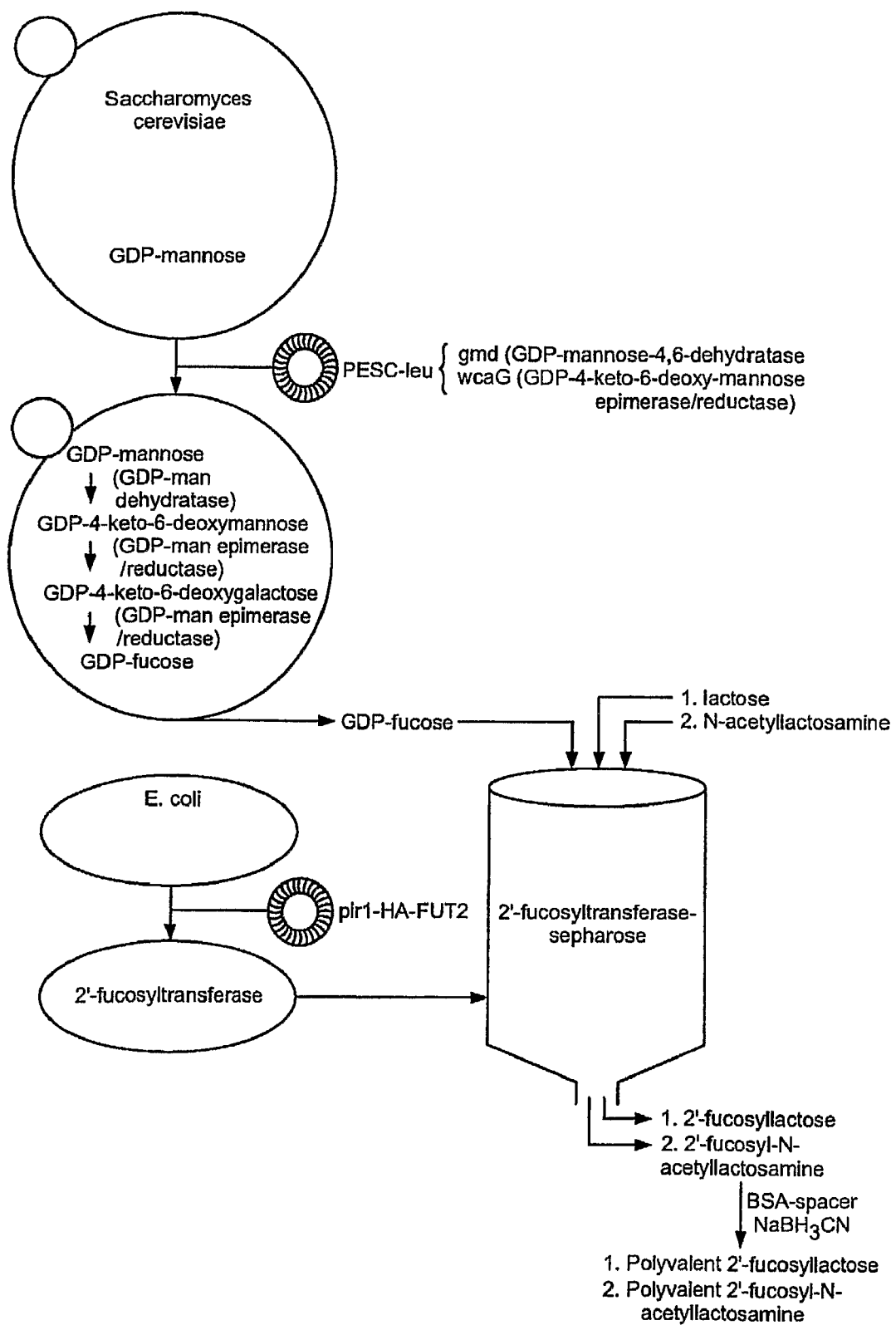
FIG. 3 schematically depicts a partially in vivo approach to synthesizing certain oligosaccharides.

The choice of glycosyl donors and acceptors, protective group strategies, and coupling conditions for formation of α-L-fucosyl (cis), and β-D-galactopyranosyl (trans) linkages will be according to the established methods of modern synthetic carbohydrate chemistry (103-105). One approach is depicted in FIG. 2 and described below.

Glycosyl don or for α-L-fucosyl residue. The critical requirement is for a donor with a "non-participating" group at O-2 (106). For this purpose 2,3,4-tri-O-benzyl-α-L-fucopyranosyl bromide is be employed, under conditions of halide ion catalysis, a method that has been successfully employed in many syntheses of α-L-fucosyl derivatives (107-111). The use of benzyl ether groups as persistent protective groups (112,113) has the additional advantage that after coupling, deprotection of donor and acceptor residues in the target compounds can be achieved at the same time by catalytic hydrogenolysis. Alternative donors, such as 1-thio, fluoride, trichloroacetimidate, or 4-pentenyl glycosides (114) can also be used.

2-Acetamido-2-deoxy-D-glucopyranose acceptors (GlcNAc acceptors). Initially, the compounds are be benzyl, 4,6-benzylidene, or allyl ether derivatives of benzyl glycosides (see FIG. 2), but the groups are manipulated so that primarily benzyl ethers will remain at the end of the synthesis. A final step of catalytic hydrogenolysis is deprotection of residues derived from both acceptor and fucosyl donor. The regioselectivity of the reductive ring opening of benzyl 2-acetamido-4,6-O-benzylidene-2-deoxy-D-glucopyranoside derivatives with lithium aluminum hydride/aluminum chloride is dependant on the steric bulk of the substituent at O-3 (115).

β-D-Galactopyranosyl donor. The primary requirement is for a "participating" group at O-2 (105). At O-1 a temporary protective group must allow introduction of a halogen atom as a leaving group in the glycosidation reaction. Bromine is preferable because of its greater reactivity (105), and the introduction should be under the mildest conditions practical. Therefore the O-1 substituent will normally be p-nitrobenzoyl, to be reacted with hydrogen bromide in dichloromethane (116). At O-2, a "participating" group is necessary for 1,2-trans-glycoside formation. O-benzoyl is favored over O-acetyl because the O-benzoyl group is less labile to basic conditions, less prone to migration, less likely to undergo unwanted ortho ester formation during coupling reactions, and easier to introduce selectively (112). At the O-2 position where linkage is desired for 2'-FL and 2'-FLNAc, a temporary protective group is necessary that can be removed after the first glycosidation without affecting other linkages or groups; the benzoyl group will perform both functions. The remaining two positions must be occupied by persistent groups (benzyl), to be removed only at the end of the synthesis.

The coupling reaction between the specially protected "internal" galactosyl donor and the protected glucosamine acceptor will employ silver triflate as promoter, in the presence of acid scavengers (collidine or tetramethylurea), and molecular sieves, i.e., standard conditions for trans glycoside coupling (117-119). Helferich conditions (120) (mercuric cyamide/mercuric bromide promoter) or Koenigs-Knorr conditions (121) (silver carbonate as insoluble catalyst) can be substituted at this step. Whichever method is used, after chromatographic purification of the product of the first glycosidation reaction, it can be useful to perbenzylate to avoid any risk of intermolecular acetyl migration during the subsequent fucosylation step.

Starting compounds, chromatography, deprotection, and structure confirmation. All the starting materials are accessible from L-fucose, D-galactose, and 2-acetamido-2-deoxy-D-glucose, via procedures described in FIG. 2. Their preparation and the coupling reactions are be followed by TLC to monitor the purification of the intermediates. The products of coupling reactions will be purified by silica gel column and preparative layer chromatography. GlcNAc acceptors are shown as benzyl glycosides for simplicity, though 2-bromoethyl glycosides or 8-methoxycarbonyloctyl glycosides, for example, may be substituted if necessary for protein conjugation. The synthesis of 2'-fucosyl-N-acetyllactosamine (110) has been described, providing experimental and spectroscopic data for preparing intermediates and characterizing products. Purity of final products is determined by TLC and HPLC, and a final purification by passage through a column of Bio-gel P-2 and/or a coupled column of cation and anion-exchange resins is performed when necessary. Structures of key intermediates and final products is confirmed by permethylation analysis and mass-spectrometry.

Analysis of Oligonucleotides

Oligosaccharides produced by any of the methods described herein can be analyzed to assess composition and structure using standard techniques. For example, GC analysis can be used to analyze sugar ratios. Briefly, a sample is transferred into a capillary tube (1 mm i.d.×35 mm) in aqueous methanol (50%). The solvent is removed during centrifugation under vacuum. The sample is dried in a vacuum desiccator over $P_2O_5$. Dry methanolic HCl (0.75 mol/L; 25 mL) and methyl acetate (5 mL) are added before the tops of the tubes are resealed in a flame. The tubes are incubated at 80° C. for 2 h and allowed to cool to ambient temperature, whereupon the top of the tube is scored and cracked open. The tube is placed under vacuum with centrifugation to remove the methanolic HCl. Internal standard (methyl heptadecanoate, 2 nmol in 5 ml methanol) is added, and the solvent is removed by vacuum centrifugation. Freshly made 50% acetic anhydride in dry pyridine (5 mL) is added, the tubes are resealed, and the acetylation allowed to proceed for 14 h at ambient temperature (the reaction is complete after 2 h). The top of the tube is scored and cracked open, whereupon an aliquot (1 µL) of the contents are injected into a gas chromatograph fitted with a 30-m DB-1 column. Peaks are detected by flame ionization. After injection into the GC, the temperature is held at 150° C. for 15 min and then raised by 4° C. per min to a maximum temperature of 300° C. Peak areas are calculated with an HP integrator. This method gives results that are suitable for determining both sugar ratios of a pure compound and absolute quantitation of sugars in a sample. This method yields consistently good results with approximately 1 µg (1 nmol) of oligosaccharide.

Products can be analyzed by mass spectrometry to assess purity and confirm structures. The number of components in a sample and their molecular weights are determined by matrix-assisted laser desorption ionization mass spectrometry. MS/MS of peracetylated sample is used to obtain compositional information on the individual components of a mixed sample. The fragmentation pattern in the fast atom bombardment mass spectrum gives some insight into the structure of a pure sample. MS/MS of derivatives can be used to obtain complete structural information even for a sample that contains a major component in the presence of appreciable impurities. Linkage of pure compounds is established by GC/MS analysis of partially O-methylated hexitols and hexosaminitol acetate (PMAAs) (123).

Polyvalent Glycoproteins

In many cases it is desirable to administer a mixture of two or more different oligosaccharides in a polyvalent form in which two or more different oligosaccharides are covalently attached to the same backbone, e.g., a protein backbone. In addition it can be desirable to administer even a single oligosaccharide in a polyvalent form, i.e., a form in which multiple copies of the same oligosaccharide are attached to a single backbone. Any suitable backbone can be used, for example, a glycan, a glycolipid, a glycoprotein, A glycosaminoglycan, a mucin or a polypeptide. Suitable backbone polypeptides have: multiple glycosylation sites (multiple Asn, Ser and or Thr residues) and low allergenic potential. In some cases it is desirable to use a polypeptide that is considered acceptable for feeding to humans. Useful backbones include: human milk proteins such as: κ-casein, α-lactalbumin, lactoferrin, bile salt-stimulated lipase, lysozyme, serum albumin, folate-binding protein, haptocorrin, lipoprotein lipase, glycosaminoglycan, mucin, lactoperoxidase, amylase, bovine milk proteins and proteins of other common foodstuffs.

Oligosaccharides can be attached to proteins using standard methods. For example, oligosaccharides are converted into p-aminophenyl glycosides, followed by diazotization and conjugation to BSA or another polypeptide using standard procedures (124,125). The p-aminophenyl glycosides can be prepared via peracetyl p-nitrophenyl glycosides (126-128). The p-aminophenyl glycosides are carefully O-deacetylated (to avoid alkaline hydrolysis) and reduced in the presence of Adams catalyst. As an alternative to the relatively unstable diazonium salts, the stable, usually crystalline isothiocyanates can be prepared and coupled to BSA or another polypeptide (e.g., milk proteins) as described (124). Alternatively, oligosaccharides with a free reducing end can be coupled to free amino groups on a protein; as found in lysine residues, or the amino terminus to form a Schiff base, which is converted into a covalent bond by reductive amination by sodium cyanoborohydride.

The attachment of the oligosaccharide to the polypeptide can be directly without spacers, or through spacers of various chain lengths. As a variety of different chemistries of spacers are available. The core N-linked glycan of a natural glycoprotein can serve as a spacer on proteins expressed in yeast.

Yeast engineered to produce proteins of choice with core N-linked glycans attached to their natural glycosylation sites (see Hamilton et al. Science 301:1244, 2003) can be used to create a neoglycoprotein as a starting point for the creation of polyfucosylated neoglycoconjugate. The following types of glycans are representative of those that could be used as a spacer (R represents the backbone, e.g., protein) and as the reducing end of the desired glycans.

Asparagine (N-Linked) Core

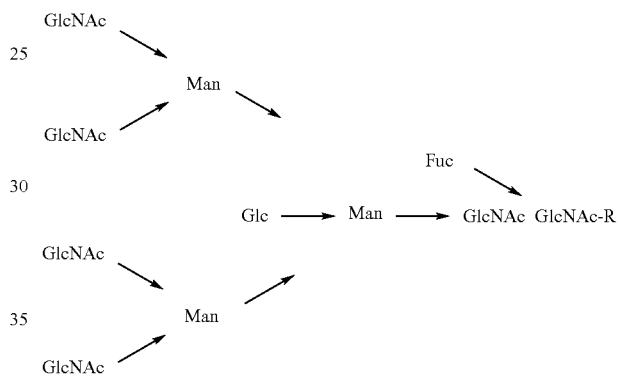

Serine/Threonine (O-Linked) Core

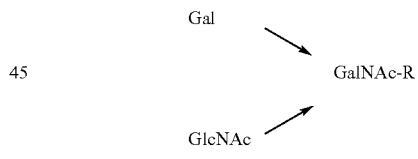

Neolacto Core
   GlcNAc Gal Glc--R

N-Linked Polylactosamine

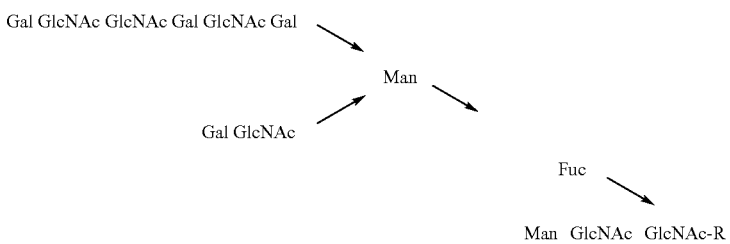

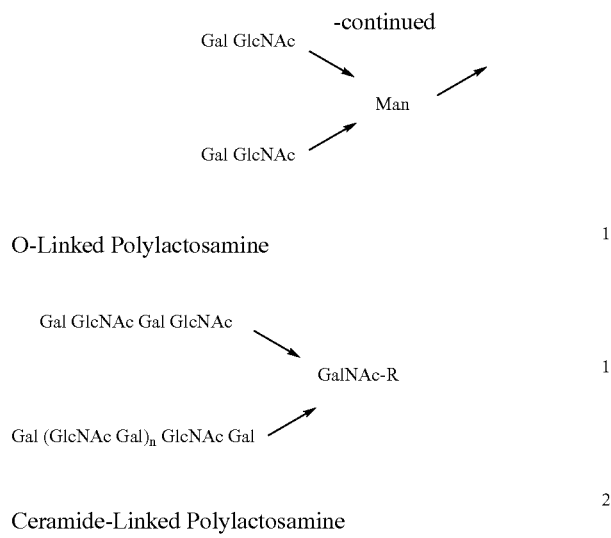

O-Linked Polylactosamine

Gal GlcNAc Gal GlcNAc
\
GalNAc-R
/
Gal (GlcNAc Gal)$_n$ GlcNAc Gal

Ceramide-Linked Polylactosamine

Gal (GlcNAC Gal)$_n$ Glc----R wherein n is 1, 2, 3, 4, 5, 6, 7 or more

To create the fucosylated forms, the neoglycoprotein is used as a substrate instead of lactose in any of the chemical, chemienzymatic, or molecular biological approaches described above. These proteins, when expressed in yeast that are engineered to express GMD, GFS, and a cell wall expressed FUT-2 will produce polyvalent forms of the H-2 epitope. An alternative approach toward the production of these polyvalent H-2 molecules would be to transfect the yeast engineered to express GMD, GFS, and a cell wall expressed FUT-2 with a plasmid-carrying gene for the human milk protein of choice and the fucosyltransferases needed for the core and glycan structure. Such a construct could produce polyvalent H-2 neoglycoproteins, which could then be isolated by *Ulex* lectin affinity chromatography.

To create the fucosylated forms, the neoglycoprotein is used as a substrate instead of lactose in any of the chemical, chemienzymatic, or molecular biological approaches described above. These proteins, when exposed to yeast that are engineered to express GMD, GFS, and a cell wall expressed FUT-1 or FUT-2 will produce polyvalent forms of the H-2 epitope; those expressing FUT3-7 or FUT-9 on the cell wall, or a combination of FUT-1 or 2 and FUT3-9 will produce the other fucosylated epitopes. An alternative approach toward the production of these polyvalent H-2 molecules would be to transfect the yeast engineered to express GMD, GFS, and a cell wall expressed fucosyltransferases with a plasmid-carrying gene for the human milk protein of choice and the fucosyltransferases needed for the core and glycan structure. Such a construct could produce polyvalent H-2 neoglycoproteins, which could then be isolated by *Ulex* lectin affinity chromatography. A third approach would be to transfect the yeast with the gene for the protein, the glycosyltransferases needed to produce the glycan core, antiporters of transport of sugar nucleotides, enzymes for synthesis of the needed sugar nucleotides and the fucosyltransferases and/or sialyltransferases needed to produce each of the fucosylated and/or sialylated structures, or the nonfucosylated, nonsialylated olifosaccharides.

Compositions

Oligosaccharides whether or not linked to a backbone can be administered as a pharmaceutical composition containing the oligosaccharides (free or linked to a backbone) and a pharmaceutically acceptable carrier, e.g., phosphate buffered saline solution, mixtures of ethanol in water, water and emulsions such as an oil/water or water/oil emulsion, as well as various wetting agents or excipients. The oligosaccharide agents can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose, diluents, lubricants, binders, disintegrating agents, and the like), etc. If desired, tablet dosages of the disclosed compositions may be coated by standard aqueous or nonaqueous techniques.

The oligosaccharide agents can be administered orally, e.g., as a tablet containing a predetermined amount of the active ingredient, pellet, gel, paste, syrup, bolus, electuary, slurry, capsule, powder, granules, as a solution or a suspension in an aqueous liquid or a non-aqueous liquid; as an oil-in-water liquid emulsion or a water-in-oil liquid emulsion, or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. The agents of the invention can also be administered by rectal suppository, aerosol tube, naso-gastric tube, direct infusion into the GI tract or stomach or parenterally.

Pharmaceutical compositions containing oligosaccharide agents can also include therapeutic agents such as antiviral agents, antibiotics, probiotics, analgesics, and anti-inflammatory agents.

The proper dosage is determined by one of ordinary skill in the art and depends upon such factors as, for example, the patient's immune status, body weight and age. In some cases, the dosage will be at a concentration similar to that found for similar oligosaccharides present in human breast milk.

The oligosaccharides agents can also be added to other compositions. For example, they can be added to an infant formula, a nutritional composition, a rehydration solution, a dietary maintenance or supplement for elderly individuals or immunocompromised individuals.

The oligosaccharides agents can be included in compositions that include macronutrients such as edible fats, carbohydrates and proteins. Edible fats include, for example, coconut oil, soy oil and monoglycerides and diglycerides. Carbohydrates include, for example, glucose, edible lactose and hydrolyzed cornstarch. Protein sources include, for example, protein source may be, for example, soy protein, whey, and skim milk.

Compositions, including nutritional compositions, containing the oligosaccharide agents can also include vitamins and minerals (e.g., calcium, phosphorus, potassium, sodium, chloride, magnesium, manganese, iron, copper, zinc, selenium, iodine, and Vitamins A, E, D, C, and B complex).

Screening and Analysis of Oligosaccharides

Oligosaccharides can be tested for their ability to bind infectious agents using the agents themselves. For example, prototype invasive *C. jejuni* strains 166-IP and 287-IP from children with inflammatory diarrhea; *C. jejuni* strain 50-SP, from a healthy child; and two *V. cholerae* strains, El Tor and Classic can be used to study the effect of oligosaccharides on *campylobacter* and *V. cholerae*.

To assess the ability of *campylobacter* and *V. cholerae* to bind to histo-blood group antigens, bacterial binding Western blot assays are performed with DIG-labeled bacteria (23,24). Neoglycoproteins of blood group antigens are applied to lanes for SDS-PAGE at $6.3 \times 10^{-10}$ M oligosaccharide per lane. Membranes are washed in TBS, immersed in a DIG-labeled bacterial suspension of 0.2 OD600 and incubated 4 h at room temperature with gentle stirring. Membranes are then washed and incubated for 1 h with the alkaline phosphatase-conjugated anti-DIG antibody, washed and stained with X-Phosphate (5-bromo-4-chloro-3-indolyl phosphate) and Tris-buffered nitroblue tetrazolium in saline (pH 9.5) substrate (Boehringer Mannheim).

$\alpha$1,2-fucosyltransferase-transfected CHO cells (CHO-FUT1), $\alpha$1,3/4-fucosyltransferase-transfected CHO cells (CHO-FUT3), and $\alpha$1,3-fucosyltransferase-transfected CHO cells (CHO-FUT4), and parental CHO cells transfected with the vector pCDM$_7$ lacking the $\alpha$1,2 FUT gene (CHO-WT) can be used to test bacterial binding and bacterial/host cell agglutination. Parental CHO cells with the vectors are used as controls.

The binding of bacteria to CHO cells transfected with the human gene for $\alpha$1,2-fucosyltransferase (FUT1), can be assessed by bacterial-cell association assay. Briefly, transfected CHO cells expressing the FUT1 fucosyltransferase needed for the synthesis of human H-type antigen ($\alpha$1,2-fucosyl residues) are grown to confluency (28). Controls are wild type CHO cells, parental CHO cells carrying only the plasmid vector, and a clone that expresses the murine UDP Gal:Gal$\alpha$1,4GlcNAc$\alpha$1,3-transferase. Monolayers are harvested and seeded into each well of an 8-chamber slide and incubated for 18 h, washed and incubated with a suspension of $9 \times 10^8$ bacteria/mL. Wells are rinsed, fixed with 10% formalin for 1 h, stained by the Warthin-Starry method, and examined under oil immersion with light microscopy, or confocal microscopy for mutant strains with the fluorescent plasmid. Identical preparations grown on round cover slips are examined by scanning electron microscopy after fixing in 2% glutaraldehyde, dehydration through a graded series of solvents, and surface gold deposition.

Ligands, such as $\alpha$1,2-fucosyl ligands and homologs are tested for their ability to inhibit binding of *campylobacter* and *V. cholerae* strains to CHO-FUT1 cells. For molecules that is bind to H-2 ligands, including anti-H-2 monoclonal antibodies (anti-H-2 MAbs) and the lectins *Ulex europaeus* (UEA I) and *Lotus tetragonolobus* (Lotus), inhibition is measured on monolayers of CHO-FUT1 cells incubated in 8-well chamber slides for 1 h with each of the $\alpha$1,2-fucosyl ligands before adding 100 µL of the bacterial suspension containing $1 \times 10^8$ bacteria/mL. For inhibition using homologs to cell surface receptors, including human milk neutral oligosaccharides (Neutral-OS), milk from secretor and non-secretor mothers, neoglycoprotein BSA-H-2 (IsoSep AB, Tullingen, Sweden), and 2'-fucosyllactose, 100 µL of the bacterial suspension are incubated with each of the homologs before being added to the cell monolayer. In both assays, after a 3 h incubation at 37° C., wells are rinsed, lysed with 1% Triton X100, and CFU (colony forming units) of bacteria per well are determined. Data are interpreted as percent inhibition of bacteria association to cells relative to positive controls to which no $\alpha$1,2-fucosyl ligands or homologs are added.

The effect of oligonucleotides and neoglycoproteins on *campylobacter* and *V. cholerae* colonization in vivo will be determined in BALB/c mice (weighing 10-20 g).

Three-week old BALB/c mice will be fed orally either BID (twice daily) or TID (thrice daily) with escalating dose of neoglycoprotein starting at 2 mg/100 µL per intake up to 200 mg/µL. Animals will be followed for 2 weeks after the last dose to evaluate for tolerance, weight, presence of diarrhea, and abnormal behavior.

Two different assays can be used to test the inhibition of *campylobacter* and cholera colonization in vivo using the inbred strain of *mus musculus* Balb/c. (1) Prophylaxis studies. In experiments designed to study the ability of neoglycoproteins to inhibit colonization prophylactically, three-week-old female mice are randomly distributed into 2 experimental plus a positive and a negative control group. The two experimental groups are challenged with $10^8$ CFU per animal. Two of the four challenge groups are treated with either the neoglycoprotein or trisaccharide 2 days before challenge, on the day of challenge, and 2 hours after challenge, either twice or three times per day. A negative control group is used to ensure that the animals are initially free from pathogens. The positive control group receives only saline. Each experimental group is compared with each other and with the saline control group.

Oligosaccharides and neoglycoproteins can be tested for their ability to clear colonization of animals who are already infected. Again, 3-week-old Balb/c mice are first infected with $10^8$ CFU of *campylobacter*, and after 7 days when the animals exhibit persistent colonization the animals will be treated with the neoglycoprotein or trisaccharide either twice or three times per day at two doses established in the tolerance and safety study.

2-Linked Fucosylated Oligosaccharides Reduce Diarrhea Due to *Campylobacter*, Caliciviruses, and Diarrhea of all Causes in Breastfed Infants Described below is a study demonstrating that a high ratio of 2-linked to non-2-linked fucosylated oligosaccharides in human milk reduces the occurrence of *Campylobacter* diarrhea and calicivirus diarrhea in breastfed infants.

A cohort of 316 mother-infant pairs was enrolled and monitored from birth to two years postpartum in San Pedro Martir, a transitional neighborhood of Mexico City. Enrollment was restricted to term, normal birthweight infants. This research was approved by institutional review boards in Mexico and Cincinnati. Written informed consent was obtained from mothers who participated. Infant illness and feeding history were collected by trained field workers who made weekly home visits. Milk samples were collected from mothers weekly in the first month, and monthly thereafter. Samples were collected in the morning by an experienced study nurse using an Egnell electric breast pump to obtain the complete content of one breast. Samples were transported on ice from the study household to the laboratory, where they were stored at −70° C. Infant stool samples were collected weekly with additional samples obtained whenever diarrhea occurred. Diarrhea samples were routinely tested for *Campylobacter jejuni*, diarrheagenic *E. coli, Shigella, Salmonella, Aeromonas*, and rotavirus, as detailed in previous publications (129, 136-138). Calicivirus testing of stool samples was later performed by enzyme immune assay (EIA) and reverse transcription-PCR; a positive result by either test was considered calicivirus positive (139-141). Diarrhea episodes were defined throughout the study as three or more watery stools within a 24-hour period or loose-to-watery bowel movements that exceeded the child's usual daily stool frequency by two or more stools as determined by a study physician. Using the severity scoring system of Ruuska and Vesikari, an episode of diarrhea was classified as moderate-to-severe if the score was ≧10 (136, 142). Classification of disease severity was based on the standardized history of each diarrhea episode recorded by a study physician, and was blind to and independent of milk oligosaccharide analysis. Diarrhea was attributed to *campylobacter* or calicivirus if the pathogen was detected in a stool sample collected during or within seven days of an episode of diarrhea. Diarrhea episodes associated with two or more pathogens were excluded from pathogen-specific analyses. Upon completion of the initial cohort study, mothers were requested to participate in a blood draw to determine maternal blood group type.

A mother-infant pair was included in the present study if they were followed in the cohort and breastfed for at least 2 weeks; the mother consented to participate in blood collection for blood group typing; and they had at least one vial of milk in storage that contained 2 mL or more of milk collected between 1-5 weeks postpartum. Reasons for exclusion were that 40 did not breastfeed and remain in the study for at least 2 weeks; 91 mothers did not consent to blood collection; and 92 had insufficient volume of milk sample in storage. A total of 93 mother-infant pairs met all three criteria and were included for study. If more than one sample was available per mother, the one closest to 30 days postpartum with at least 2 mL volume was selected.

Milk samples were transported to Boston and analyzed as described previously(143). Milk oligosaccharides were isolated, perbenzoylated, and resolved by reversed-phase HPLC (C-8) with an acetonitrile/water gradient and detected at 229 nm. This chromatography system produces eight major peaks in human milk samples, which correspond to the most common oligosaccharides of human milk: four 2-linked fucosylated oligosaccharides (lacto-N-fucopentaose I [LNF-I], 2'-FL, lacto-N-difucohexaose [LDFH-I] and lactodifucotetraose [LDFT]); two fucosylated oligosaccharides that are not 2-linked (LNF-II and 3-fucosyllactose [3-FL]); and their two precursors (lacto-N-tetraose [LNT] and lacto-N-neotetraose [LNneoT]). These eight oligosaccharides are homologs of Lewis histo-blood group antigens, respectively: H-1, H-2, $Le^b$, $Le^y$, $Le^a$, $Le^x$, and types 1 and 2 precursors. Detection of oligosaccharides in human milk samples was not adversely affected by storage or freeze-thaw.

Statistical Analysis

The primary analysis focused on the incidence of diarrhea during breastfeeding defined as the total number of cases of diarrhea that occurred during breastfeeding per 100 child-months of breast-feeding. Child-months of breastfeeding was calculated as the sum of all months spent breastfeeding, from birth to the end of breastfeeding (or termination from study, whichever occurred sooner). A secondary analysis was conducted of the incidence of diarrhea during post-breastfeeding child-months, i.e., from the end of breastfeeding to termination from study. Time during diarrheal illness was not included in the denominator used to calculate incidence rates. Study outcomes were defined as the rates of diarrhea associated with *C. jejuni*, calicivirus, all causes of diarrhea, and all causes of moderate-to-severe diarrhea. The major independent variables were the specific and total 2-linked fucosylated oligosaccharides characterized in terms of concentration in milk (mmol/L) and percent of milk oligosaccharide (the quantity of specific or total 2-linked fucosylated oligosaccharide divided by the sum of the eight oligosaccharides measured). The percent of milk oligosaccharide measure was used to correct for variability in concentrations due to lactation physiology, sampling, collection, storage, and testing.

Correlations were analyzed among oligosaccharide measures. The associations between milk oligosaccharide measures and rates of diarrhea outcomes were examined using a generalized linear model with a Poisson link function. This model was selected as optimal for analysis of incidence rates with one or more outcomes per person, accounting for variable lengths of follow-up time. Potential interactions or confounding by factors shown in table 1 were analyzed in relation to milk oligosaccharide measures and rates of infant diarrhea. Significant ($P<0.05$) risk factors associated with the rate of infant diarrhea in univariate and/or multivariate models were the percent of infant feedings that were breast milk (calculated from weekly follow-up data for the duration of breastfeeding as the number of breast milk feedings divided by the total number of feedings in the past 24 hours), infant birth order, maternal age, and maternal ABO blood group type. These factors were included in multiple regression models but they were not associated with milk oligosaccharide values and did not confound the associations between oligosaccharide measures and diarrhea outcomes. Thus, final regression models included only specific or total 2-linked fucosylated oligosaccharide expressed as a percent of milk oligosaccharide in relation to diarrhea outcomes. In addition to analysis of milk oligosaccharides as continuous variables, the dose-response pattern of the data was further examined by classifying mother-infant pairs into low, intermediate, and high tertiles (n=31 per group) of milk oligosaccharide values, with rates of infant diarrhea calculated by group.

Study Population

The 93 mother-infant pairs in this study were monitored for 857 breastfeeding infant-months and 765 post-breastfeeding infant-months between birth and 2 years of age. These 93 mother-infant pairs were compared to the 183 mothers in the cohort who were not included in this study but had breastfed their infants for at least 2 weeks; they were comparable regarding the incidence of infant diarrhea during breastfeeding and all sociodemographic, hygiene, and infant factors (table 1), except that mothers included in this study breastfed longer (median duration 9 vs 5 months, $P<0.01$) and were more likely to complete a secondary education or higher ($P<0.01$) than those not included. Analysis of these factors found that they were not associated with milk oligosaccharide levels and were not confounding. These differences were thus unlikely to affect the internal validity of this study. Among the 93 study pairs, the mean percent of feedings that were breast milk was 49% during the breastfeeding period; none practiced exclusive breastfeeding. In addition to their own mother's milk, study infants were given differing amounts of formula, juice, tea, water, solid foods, and gruel. Two-thirds of mothers were O blood type; nearly three-quarters were Lewis positive secretors (Le a−b+) and one-quarter were Lewis negative secretors (Le a−b−). The serologic classification for two mothers was Le a+b−, which is considered to indicate obligate non-secretors. However, since the milk from these two mothers contained 2-linked fucosylated oligosaccharide, inconsistent with being a non-secretor, the discrepancy between milk and blood group phenotypes was resolved by classifying the blood group as indeterminate (Table 1).

TABLE 1

Characteristics of the 93 breastfeeding mother-infant pairs

| Characteristic | | Measure | Value |
|---|---|---|---|
| Number of people in the household | | Median (range) | 5 (3-11) |
| Kept animals in the household | | No. (%) | 66 (71%) |
| Age of mother (years) | | Median (range) | 23 (15-41) |
| Maternal education: | None/Elementary | No. (%) | 42 (45%) |
| | Middle school | | 31 (33%) |
| | High school and beyond | | 20 (22%) |
| Primiparous mother | | No. (%) | 31 (33%) |
| Duration of breast-feeding (months) | | Median (range) | 9 (0.7-24) |
| Percent of infant feedings that were breast milk | | Median (range) | 49 (4-82%)* |
| Maternal Lewis blood group: | a–b+ | No. (%) | 67 (72%) |
| | a–b– | | 24 (26%) |
| | indeterminate | | 2 (2%) |
| Maternal ABO blood group: | O | No. (%) | 62 (67%) |
| | A | | 18 (19%) |
| | B | | 12 (13%) |
| | AB | | 1 (1%) |
| Male infant | | No. (%) | 43 (46%) |
| Age in months at diarrhea outcomes during breastfeeding: | | Median (range) | |
| All diarrhea (234 cases): 6.9 (0.1, 23.4) | | | |
| Moderate-to-severe (77 cases): 6.7 (0.1, 20.3) | | | |
| *Campylobacter* (31 cases): 9.2 (1.6, 15.6) | | | |
| Calicivirus (16 cases): 9.1 (1.2, 14.4)** | | | |

Milk Analysis

A single milk sample was analyzed for each mother; all analyzed samples were collected 1-5 weeks (median, 3 weeks) postpartum in a standardized manner to avoid sampling variation. The representativeness of this sample for the course of lactation was analyzed using longitudinal data from 11 Mexican secretor mothers. The 2-linked fucosylated oligosaccharide measured in the milk sample collected at 3 weeks postpartum was highly correlated ($r=0.73$) with the average of the same measure in milk collected from each mother at 3, 6, 9, and 12 months of lactation (144).

Milk oligosaccharide concentrations ranged from 1.0 to 36.1 mmol/L. Total 2-linked fucosylated oligosaccharide concentrations ranged from 0.8 to 20.8 mmol/L (50 to 92 percent of milk oligosaccharide) (Table 2). The most commonly occurring specific 2-linked fucosylated oligosaccharides were 2'-FL (34 percent of milk oligosaccharide) and LNF-I (25 percent of milk oligosaccharide). The milk of the 24 Le a–b– mothers had significantly ($P<0.05$) higher percent of total 2-linked fucosylated oligosaccharide compared to the 67 Le a–b+ mothers (80 vs 71 percent of total, respectively). The 2-linked fucosylated oligosaccharides, whether analyzed as milk concentrations or percent of milk oligosaccharide, were not associated with maternal sociodemographic factors or ABO blood group. Correlations between specific oligosaccharides expressed as milk concentrations ranged from $r=-0.1$ to $+0.8$, and as percent of milk oligosaccharide ranged from $r=-0.5$ to $+0.6$.

TABLE 2

Characterization of the concentration (mean ± SD) and the percent of specific and total α1,2-linked fucosylated oligosaccharides in maternal milk.

| Milk Oligosaccharide | Concentration (mmol/L) | | Percent of milk oligosaccharide | |
|---|---|---|---|---|
| | Mean ± SD | Range | Mean ± SD | Range |
| lacto-N-fucopentaose I (LNF-I) | 3.21 ± 1.75 | 0, 7.0 | 25.1 ± 9.9 | 0, 43.7 |
| 2'-fucosyllactose (2'-FL) | 3.85 ± 1.04 | 0.5, 6.2 | 33.7 ± 10.4 | 0.05, 66.7 |
| lacto-N-difucohexaose I (LDFH-I) | 1.26 ± 1.00 | 0, 5.2 | 9.5 ± 5.7 | 0, 25.4 |
| lactodifucotetraose (LDFT) | 0.70 ± 0.72 | 0.03, 5.0 | 5.1 ± 3.4 | 0.01, 16.9 |
| Total 2-linked fucosyl oligosaccharide | 9.02 ± 3.23 | 0.78, 20.8 | 73.3 ± 8.8 | 50.5, 92.3 |
| Total milk oligosaccharide+ | 12.44 ± 4.8 | 1.0, 36.1 | 100 | |

*Percent of milk oligosaccharide is the quantity of each specific oligosaccharide divided by the total quantity of the milk oligosaccharides measured in this study.
+Total milk oligosaccharide includes eight oligosaccharides: the four 2-linked fucosylated oligosaccharides, two non-2-linked fucosylated oligosaccharides (3-FL and LNF II) and their two precursors.

Association with Diarrhea

During breastfeeding, a total of 234 diarrhea episodes were identified (median, 2 diarrhea episodes per child; range, 0-12 episodes per child), of which a total of 77 (33%) diarrhea episodes were moderate-to-severe. The incidence of diarrhea was 28.8 cases per 100 child-months of breastfeeding and of moderate-to-severe diarrhea was 9.5 cases per 100 child-months of breastfeeding. Among all diarrhea episodes, 40 were associated with *C. jejuni,* 25 with calicivirus, 10 with enteropathogenic *E. coli,* 9 with rotavirus, 5 with *shigella,* and 4 with stable toxin-associated *E. coli.* Excluding diarrhea episodes with detected co-infections, 31 diarrhea episodes were associated with *C. jejuni* in 22 children, and 16 episodes of diarrhea were associated with calicivirus in 13 children.

Figure 6A:
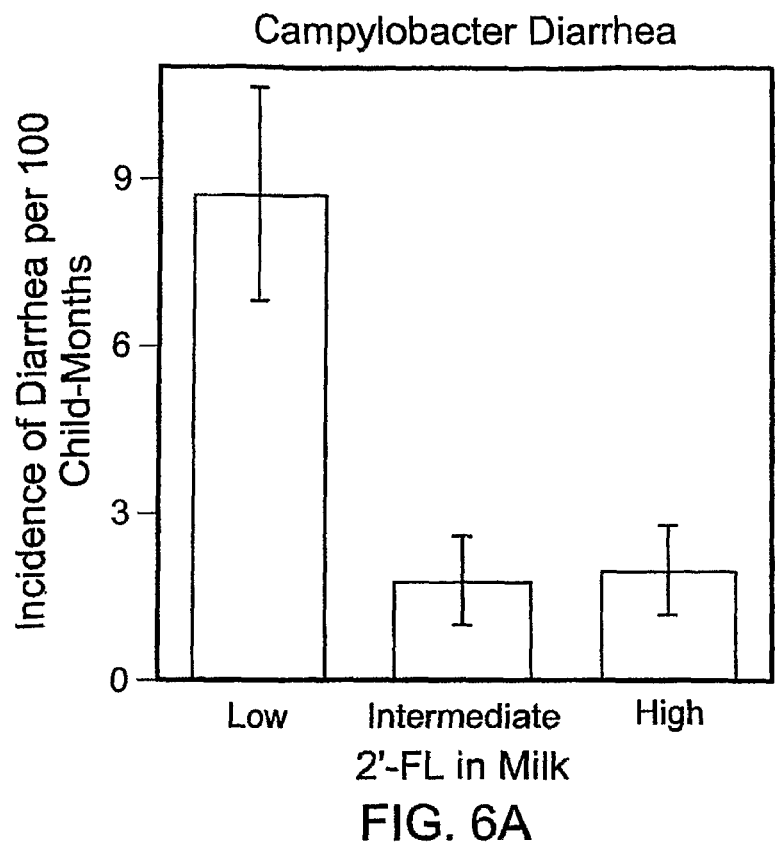
FIGS. 6A, 6B, and 6C are a series of graphs illustrating the incidence of *C. jejuni* diarrhea, calicivirus diarrhea and moderate to severe diarrhea of all causes in study children whose mother's milk contains low, intermediate, or high relative amounts of (FIG. 6A) 2'-FL, (FIG. 6B) LDFH-I, and (FIG. 6C) total 2-linked fucosylated oligosaccharide as a percent of milk oligosaccharide. The bars indicate the cause-specific incidence rates of diarrhea in each group; the vertical lines indicate the standard error. The low, intermediate, and high groups each represent the oligosaccharide values of a tertile (n=31) of the study population. For 2'-FL, the percent of milk oligosaccharide values by group: low (<0.29), intermediate (0.29-0.36), and high (>0.37). Compared to the low group, *campylobacter* incidence in the intermediate and high groups were both significantly (P<0.01) less. For LDFH-I, the percent of milk oligosaccharide values by group: low (<0.07), intermediate (0.07-0.11), and high is (>0.12). Compared to the low group, calicivirus incidence in the high group was significantly (P=0.02) less. For total 2-linked fucosylated oligosaccharide, the percent of milk oligosaccharide values in each group: low (<0.72), intermediate (0.72-0.77) and high (>0.77). Compared to the low group, incidence of moderate-to-severe diarrhea in the intermediate and high groups were both significantly (P<0.01) less.
Figure 6B:
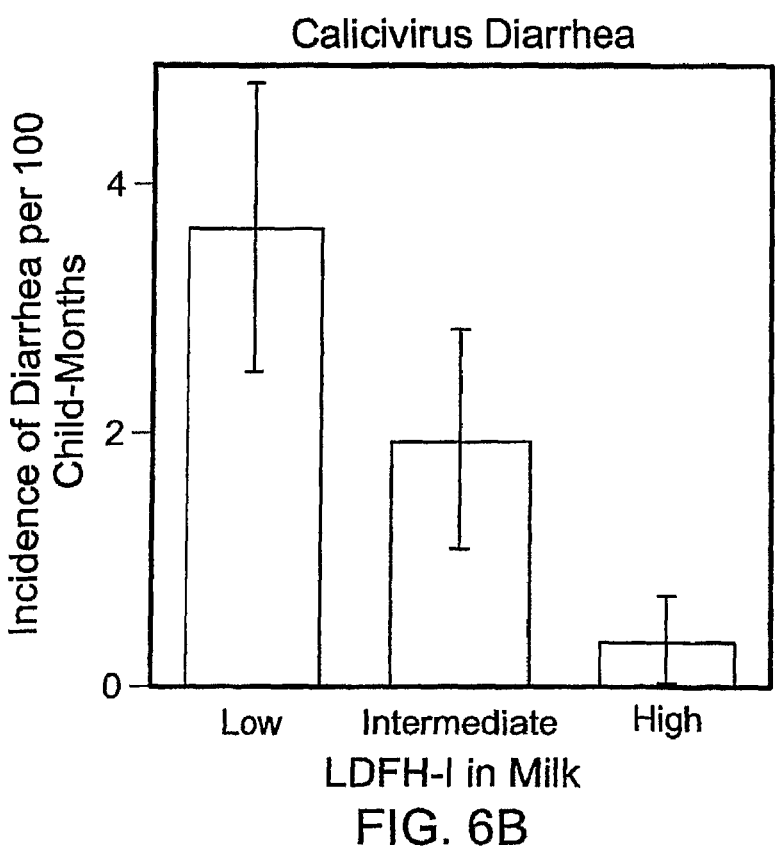

Rates of *C. jejuni* diarrhea during breastfeeding were inversely associated (P=0.004) with 2'-FL as a percent of milk oligosaccharide (Table 3), and directly associated (P=0.047) with LDFH-I as a percent of milk oligosaccharide, but association with LDFH-I did not persist after controlling for 2'-FL in regression models. 2'-FL as a percent of milk oligosaccharide, however, remained significantly (P<0.05) inversely associated with rates of *C. jejuni* diarrhea, whether in univariate or multivariate models. Analyzed categorically, the group with low 2'-FL as a percent of milk oligosaccharide had significantly (P<0.01) higher rates of *Campylobacter* diarrhea during breastfeeding than each of the medium and high 2'-FL groups (FIG. 6A). For calicivirus diarrhea during breastfeeding, several milk oligosaccharides tended towards protective associations (Table 3), but only LDFH-I was significant (P=0.012). The inverse association between LDFH-I as a percent of milk oligosaccharide and calicivirus diarrhea had a visible dose-dependent relationship (FIG. 6B).

TABLE 3

Univariate analyses of specific α1,2-linked fucosylated oligosaccharides as a percent of milk oligosaccharide and protection against *C. jejuni*-associated diarrhea and calicivirus-associated diarrhea in study children, by Poisson regression*

| Milk Oligosaccharide | Campylobacter† β (SE) | P | Caliciviruses† β (SE) | P |
|---|---|---|---|---|
| LNF-I | −0.51 (1.75) | 0.772 | 3.30 (2.66) | 0.215 |
| 2'-FL | −5.60 (1.93) | 0.004 | 3.77 (2.14) | 0.078 |
| LDFH-I | 5.87 (2.95) | 0.047 | −13.32 (5.33) | 0.012 |
| LDFT | 3.09 (4.74) | 0.514 | −16.82 (11.00) | 0.126 |

*Each model included only one independent variable, a specific 2-linked fucosylated oligosaccharide as percent of milk oligosaccharide, and pathogen-specific diarrhea as the dependent variable.
Negative beta coefficients indicate protection. Significant protective associations are in bold type.
†22 subjects had 31 cases of *campylobacter* diarrhea, 13 subjects had 16 cases of calicivirus diarrhea.

Figure 6C:
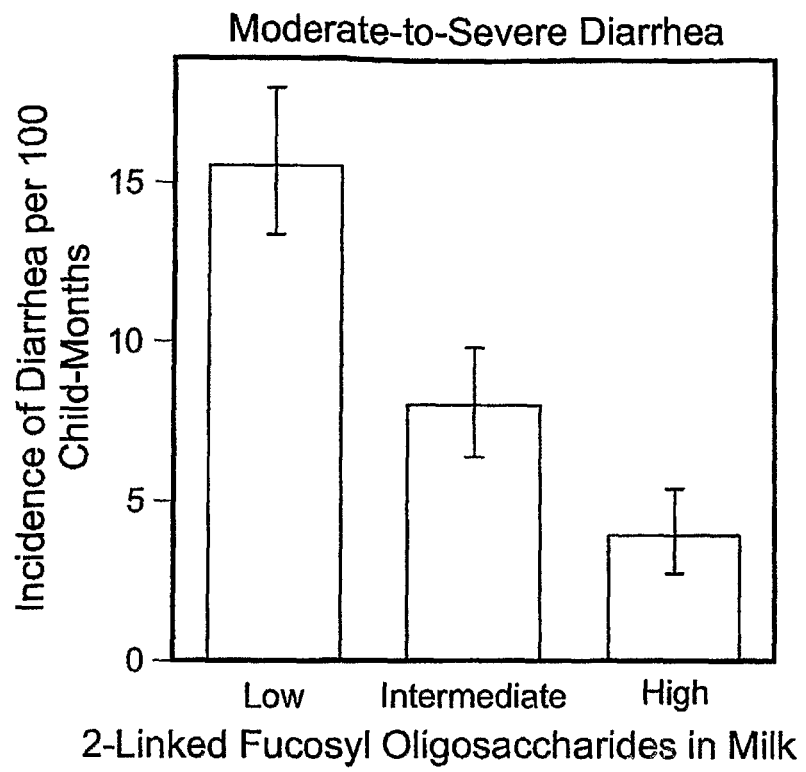

A significant inverse association ($\beta=-3.9\pm1.2$ (SE[β], P=0.001) was found by Poisson regression between total 2-linked fucosylated oligosaccharide as a percent of milk oligosaccharide and rates of all moderate-to-severe diarrhea during breastfeeding, but no association was found with all diarrhea. Whether analyzed as a continuous or categorical variable, total 2-linked fucosylated oligosaccharide in milk had an inverse, dose-dependent relationship with moderate-to-severe diarrhea (FIG. 6C). The inverse associations between 2-linked fucosylated oligosaccharides of milk and diarrhea outcomes persisted for the duration of the breastfeeding, analyzed by stratifying on age while breastfeeding (0-5, 6-12, 13-18, and 19-24 months). Exclusion of the 6 study children with <1 month duration of breastfeeding did not alter the observed associations between milk oligosaccharides and diarrhea outcomes.

In the post-breastfeeding period, a total of 89 children continued in the study and experienced 188 diarrhea episodes, 60 moderate-to-severe diarrhea episodes, and 36 *campylobacter* diarrhea episodes (calicivirus testing was not conducted for the post-breastfeeding period). No associations were observed between milk oligosaccharides and post-breastfeeding diarrhea outcomes.

In this study of breastfed Mexican infants, we found that low levels of specific 2-linked fucosylated oligosaccharides in human milk were significantly associated with increased rates of pathogen-specific infant diarrhea. *C. jejuni* and caliciviruses, excluding co-infections, together accounted for 20% of all diarrhea episodes in our study population. A low level of 2'-FL as a percent of milk oligosaccharide was associated with a high rate of *C. jejuni* diarrhea in breastfed infants. Similarly, lower levels of LDFH-I as a percent of milk oligosaccharide had a dose-dependent association with higher rates of calicivirus diarrhea. We also found that lower levels of total 2-linked fucosylated oligosaccharide as a percent of milk oligosaccharide had a dose-dependent association with higher rates of moderate-to-severe diarrhea of all causes. The association between milk oligosaccharide measured during the first month postpartum and diarrhea in breastfed infants persisted through the course of breastfeeding, but not after termination of breastfeeding. This observation was consistent with our proposed mechanism of protection: the presence of milk oligosaccharide in the infant gastrointestinal tract to inhibit pathogen binding. In our study population, all maternal milk contained some 2-linked fucosylated oligosaccharide, but there was a wide range of expression, with specific and total 2-linked oligosaccharide measured on a continuous scale. The association between milk oligosaccharide and diarrhea in breastfed infants was observed only for percent of milk oligosaccharide, suggesting the importance of a denominator to correct for variability in recovery of oligosaccharide that occurred despite standardized milk sample collection and laboratory methods.

The human milk oligosaccharides measured in this study are Lewis epitopes, products of the same genes that control maternal Lewis histo-blood group type. Blood group types are the result of genetic polymorphisms that determine oligosaccharide-containing glycoconjugate expression on host cell surfaces. Associations have been previously reported between histo-blood group type and differing susceptibility to bacterial and viral diseases. Glass et al. showed that O blood group individuals have increased susceptibility to cholera (145). P blood group type has been associated with susceptibility to hemolytic uremic syndrome (146). Ikehara et al. found an association between Lewis and secretor histo-blood group genotypes and risk of infection with *Helicobacter pylori* (147). Hutson et al. reported that O blood group individuals have increased susceptibility to Norwalk virus (148). Influenza virus binding has been shown to vary in relation to host blood group antigens (149).[3] Further, Raza et al reported that secretor children have increased risk of hospitalization for respiratory infections due to influenza viruses A and B, rhinoviruses, respiratory syncytial virus, and echoviruses (150).

This study is unique in examining the mother-infant dyad. Phenotypic variation in the relative quantities of 2-linked fucosylated oligosaccharides in mothers' milk determines the protection offered to breastfed infants. Because the same genotype that produces milk oligosaccharides in the mother is expected to produce cell surface receptors that increase risk in the infant, the lack of control for infant susceptibility is likely to have biased our results such that the true association between milk oligosaccharides and protection against disease is stronger than observed. Further, we note that certain major endemic pathogens not included in this study, e.g., ST-associated *E. coli* (130, 134, 135) are also inhibited by 2-linked fucosylated oligosaccharides, while others, e.g., rotavirus, are inhibited by human milk glycoconjugates encoded by products of genes other than the secretor and Lewis genes (129). Thus, the association we have described provides only a glimpse into the potential protective role of the innate immune system of human milk.

A growing body of research suggests that common mechanisms of pathogenesis may exist between some bacterial and viral pathogens.[17-20,33-35,37] We have found that both *C. jejuni*, a bacterium, and caliciviruses bind to 2-linked fucosylated oligosaccharides.[17-19] Fucosylated oligosaccharide milk fractions inhibit *C. jejuni* adherence to human epithelial cells in vitro and colonization in experimental mice, and 2'-FL inhibits *C. jejuni* binding to human intestinal mucosa ex vivo (131). Further, we also found that Chinese hamster ovary cells transfected with a human fucosyltransferase gene bind *C. jejuni*, and that this binding is inhibited by Lewis epitopes containing 2'-FL. Our studies with caliciviruses have shown that Norwalk virus-like particles bind to tissue sections of the gastro-duodenal junction from secretors but not from non-secretors (132), and that binding is blocked by milk from a secretor (133). Volunteers challenged with Norwalk virus become symptomatically infected only if they are secretors. Consistent with our finding that LDFH-1 oligosaccharide (an Le$^b$ oligosaccharide homolog) is associated with protection against calicivirus diarrhea, our laboratory data suggest that Le$^b$ epitopes and other 2-linked fucosylated oligosaccharide structures inhibit binding by common strains of caliciviruses.

Potential limitations of this study should be considered. A single milk sample collected in a standardized manner from each mother was analyzed in relation to infant diarrhea for the duration of breastfeeding. Our data indicate, however, that the expression of 2-linked fucosylated milk oligosaccharide in the first month is highly correlated with its expression across lactation. In this study, we found oligosaccharide associated with protection against moderate-to-severe but not mild diarrhea. With a larger sample size and analysis of multiple samples across lactation, future studies might be better able to determine whether milk oligosaccharides protect against mild diarrhea. Inclusion of mothers in this study required sufficient milk volume in cryogenic storage and participation in an additional blood draw. As a result, mothers in our study had significantly longer duration of breastfeeding and a higher educational level than others in the original cohort, but these factors were not associated with the milk oligosaccharides under study.

Our findings suggest that heterogeneous expression of oligosaccharides in human milk provides infants with varying degrees of protection against specific pathogens, consistent with the concept that heterogeneous expression of oligosaccharide epitopes in infants underlies their individual susceptibility to different pathogens. Because many of the oligosaccharides found in human milk are unique, this study supports the importance of breastfeeding. In summary, the associations observed from this study provide initial clinical evidence that human milk oligosaccharides may offer clinically relevant protection against diarrhea, and suggests the potential for oligosaccharides to form the basis of oral agents with potent antibacterial and antiviral activity.

Figure 7:
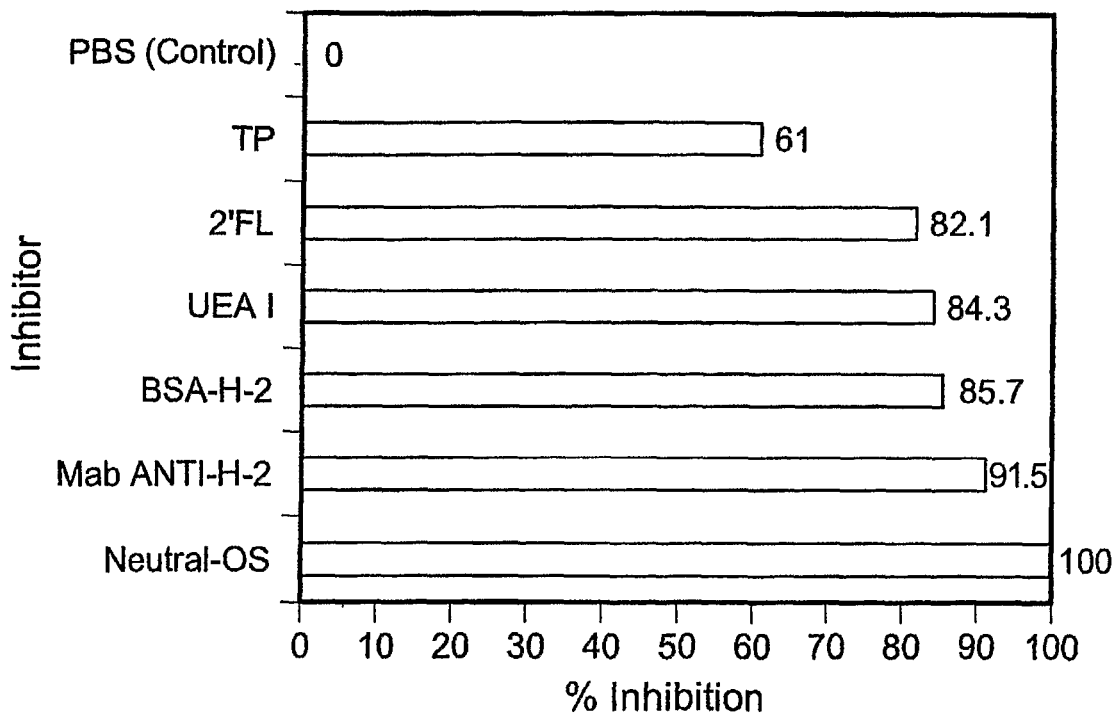
FIG. 7 is a graph presenting the results of a study showing the inhibition of *Campylobacter* binding to FUT1-CHO cells by H-2 ligands and H-2 mimetics and human milk oligosaccharides.
Figures 8, 9A:
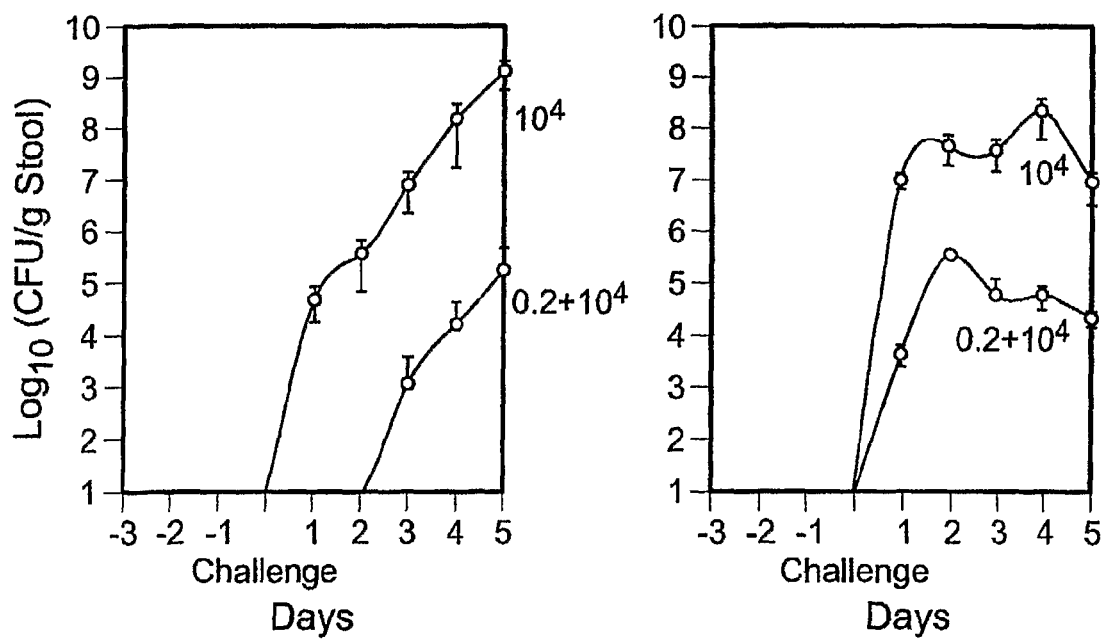
FIG. 8 is a chart presenting the results of a study showing that cell agglutination is induced by invasive *Campylobacter* strain 287ip on transfected CHO cells carrying FUT1 (1,2 Fuc), FUT3 (1,3/1,4 Fuc), and FUT4 (1,3 Fuc) gene.
FIGS. 9A and 9B are a pair of graphs depicting the results of an study showing inhibition of *Campylobacter* colonization in BALB/c mice fed with 2 mg of milk fucosylated oligosaccharides given during challenge with $10^4$ and $10^8$ CFU of bacteria (left). Ex vivo assays of inhibition of human gut colonization of *Campylobacter* with 2'-fucosyllactose (2'-FL) and milk fucosylated oligosaccharides (OS).
Figure 9B:
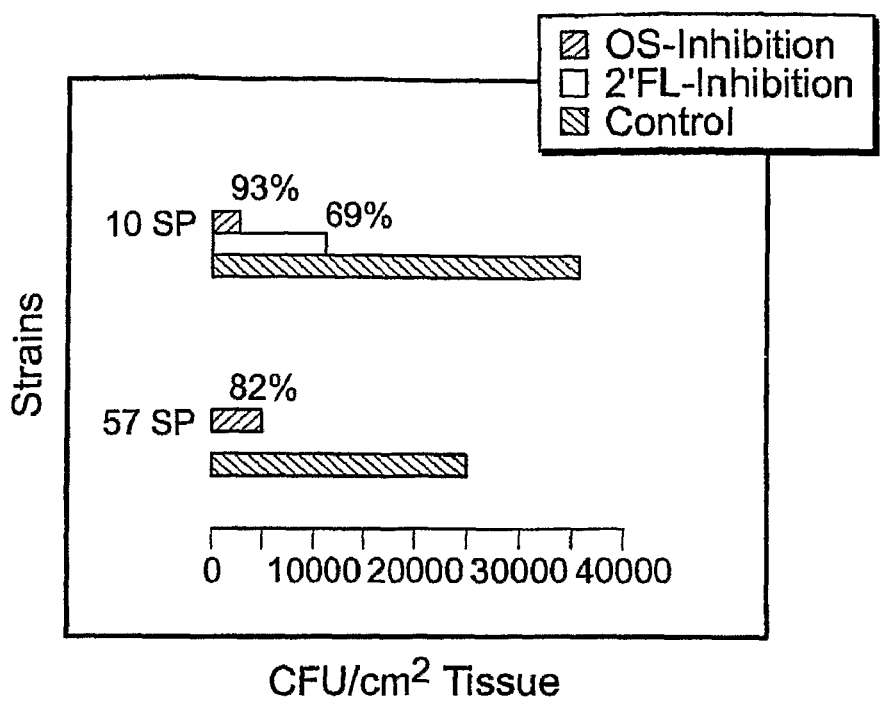

2-Linked Fucosylated Oligosaccharides Reduce *Campylobacter* and Cholera Adherence to Cells The specific binding of *campylobacter* in HEp2 cells is inhibited by fucosylated carbohydrate moieties containing the H(O) blood group epitope (Fucα1,2Galβ1,4GlcNAc). Studies of *campylobacter* binding to histo-blood group antigens as neoglycoproteins immobilized in nitro-cellulose membranes demonstrated a high avidity for the H-2 antigen as confirmed by specific inhibition with monoclonal antibodies. In studies on the mechanism of adherence, *C. jejuni*, which normally does not bind to Chinese hamster ovary (CHO) cells, bound avidly when the cells were transfected with a human α1,2-fucosyltransferase gene that caused over-expression of H-2 antigen. Similarly, *V. cholerae* adheres to transfected but not to parental cells. This binding was specifically inhibited by H-2 ligands (*Ulex europaeus* lectin, *Lotus tetragonolobus* lectin, and H-2 monoclonal antibody), H-2 mimetics, and human milk oligosaccharides (FIG. 7). Invasive *campylobacter* 287-IP binds to FUT1, but not FUT3 or FUT4-transfected CHO cells (FIG. 8). In experimental models, human milk oligosaccharides inhibited *campylobacter* colonization in mice in vivo and in human intestinal mucosa ex vivo. (FIGS. 9A and 9B).

Figure 10A:
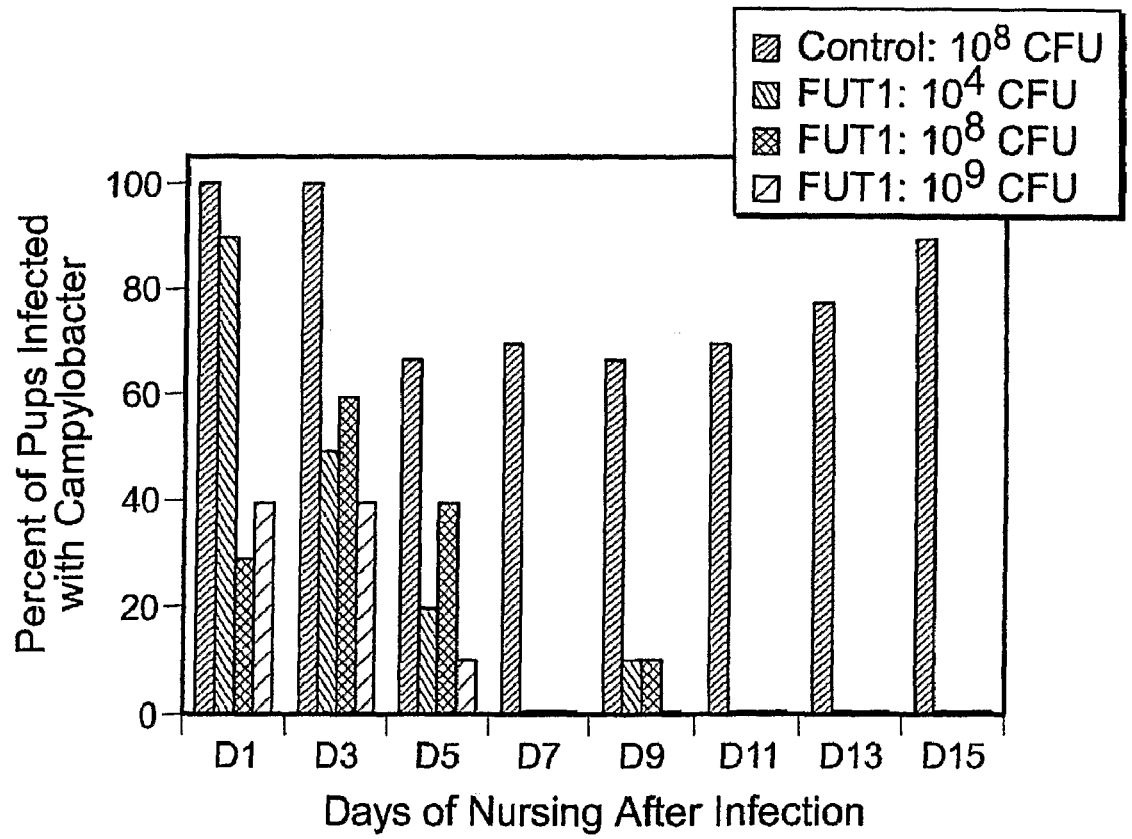

The role of milk α1,2 glycoconjugates in passive protection against *campylobacter* infection was evaluated in litters of B6-SJL transgenic female mice carrying the human α1,2-fucosyltransferase gene (FUT2) with a whey promoter that induces the expression of histo-blood group antigens primarily in mammary gland during lactation, and thus, in milk. As a control, non-transgenic parental mice were used. Suckling mice were challenged with $10^4$, $10^6$ and $10^8$ CFU of *C. jejuni* and were returned to the dams. Gut colonization was monitored for 15 days. Up to 90% of non-transgenic litters remained colonized during follow-up. Colonization of transgenic mice was transient and the time of colonization was directly related to the inoculum (FIGS. 10A and 10B). These experiments strongly support the role of α1,2-linked fucosylated glycoconjugates of milk in protection against *campylobacter* infection, and suggest that the main intestinal ligands for *campylobacter* are the H-2 histo-blood group antigens. Milk fucosyloligosaccharides and specific fucosyl α1,2-linked molecules inhibit this binding. Preliminary experiments of cholera infection in suckling pups from pWAP FUT1 transgenic dams expressing H(O) experiments of cholera infection in suckling pups from pWAP FUT1 transgenic dams expressing H(O) antigen in mammary gland, demonstrated, as with *campylobacter*, a significant reduction in colonization with an inoculum of $10^8$ CFU and a significant reduction in mortality with an inoculum of $10^{10}$ CFU when compared with non-transgenic controls. Our data strongly support the role of α1,2-fucosyl glycoconjugates in the protection against *campylobacter* infection and suggest that the main intestinal ligands for *campylobacter* are the H-2 histo-blood group antigens.

REFERENCES

1. Newburg D S. Human milk glycoconjugates that inhibit pathogens. Curr Med Chem 1999; 6:117-127.
2. Ruiz-Palacios G, Cervantes L E, Ramos P, Prieto P A, Newburg D S. *Campylobacter jejuni* binds intestinal H(O) antigen (Fucα1,2Galb1,4GlcNAc), and fucosyloligosaccharides of human milk inhibit its binding and infection. J Biol Chem 2003; 278: 14112-14120.
3. Huang P. Farkas T, Marionneau S, et al. Noroviruses bind to human ABO, Lewis and secretor histo-blood group antigens: Identification of four distinct strain-specific patterns. J Infect Dis 2003
4. Morrow A L, Ruiz-Palacios G M, Altaye M, et al. Human milk oligosaccharide blood group epitopes and innate immune protection against diarrhea in breast-fed infants. Under revision for J Pediatrics.
5. Marionneau S, Ruvoen N, Le Moullac-Vaidye B, et al. Norwalk virus binds to histo-blood group antigens present on gastroduodenal epithelial cells of secretor individuals. Gastroenterology 2002; 122: 1967-1977.
6. Newburg D S, Pickering L K, McCluer R H, Cleary T G. Fucosylated oligosaccharides of human milk protect suckling mice from heat-stabile enterotoxin of *Escherichia coli*. J Infect Dis 1990; 162: 1075-1080.

7. Newburg D S. Bioactive components of human milk: Evolution, efficiency, and protection. Adv Exp Med Biol 2001; 501: 3-10.
8. American Academy of Pediatrics. Breastfeeding and the use of human milk. American Academy of Pediatrics. Work Group on Breastfeeding. Pediatrics 1997; 100: 1035-1039.
9. WHO Collaborative Study Team. Effect of breastfeeding on infant and child mortality due to infectious diseases in less developed countries: a pooled analysis. WHO Collaborative Study Team on the Role of Breastfeeding on the Prevention of Infant Mortality. Lancet 2000; 355: 451-455.
10. Kramer M S, Chalmers B, Hodnett E D, et al. Promotion of Breastfeeding Intervention Trial (PROBIT): a randomized trial in the Republic of Belarus. JAMA 2001; 285: 413-420.
11. Morrow A L, Guerrero M L, Shults J, et al. Efficacy of home-based peer counselling to promote exclusive breastfeeding: a randomised controlled trial. Lancet 1999; 353: 1226-1231.
12. Arifeen S, Black R E, Antelman G. Baqui A, Caulfield L, Becker S. Exclusive breastfeeding reduces acute respiratory infection and diarrhea deaths among infants in Dhaka slums. Pediatrics 2001; 108: E67.
13. Hanson L A, Ceafalau L, Mattsby-Baltzer I, et al. The mammary gland-infant intestine immunologic dyad. Adv Exp Med Biol 2000; 478: 65-76.
14. Pickering L K, Granoff D M, Erickson J R, et al. Modulation of the immune system by human milk and infant formula containing nucleotides. Pediatrics 1998; 101: 242-249.
15. Horton S, Sanghvi T, Phillips M, et al. Breastfeeding promotion and priority setting in health. Health Policy Plan 1996; 11: 156-168.
16. Morrow A L, Pickering L K. Human milk protection against diarrheal disease. Semin Pediatric Infectious Diseases 1994; 5: 236-242.
17. Hamosh M. Bioactive factors in human milk. Pediatr Clin North Am 2001; 48: 69-86.
18. Garofalo R P, Goldman A S. Expression of functional immunomodulatory and anti-inflammatory factors in human milk. Clin Perinatol 1999; 26: 361-377.
19. Noguera-Obenza M, Cleary T G. The role of human milk secretory IgA in protecting infants from bacterial enteritis. Adv Nutr Res 2001; 10: 213-229.
20. Morrow A L, Pickering L K. Human milk and infectious diseases. In: Long S S, Pickering L K, Prober C G, eds. Principles and Practice of Infectious Diseases. Second ed. New York: Churchill Livingstone, 2002.
21. Viverge D, Grimmonprez L, Cassanas G, Bardet L, Solere M. Discriminant carbohydrate components of human milk according to donor secretor types. J Pediatr Gastroenterol Nutr 1990; 11: 365-370.
22. Thurl S, Henker J, Siegel M, Tovar K, Sawatzki G. Detection of four human milk groups with respect to Lewis blood group dependent oligosaccharides. Glycoconj J 1997; 14: 795-799.
23. Zopf D, Roth S. Oligosaccharide anti-infective agents. Lancet 1996; 347: 1017-1021.
24. Newburg D S. Oligosaccharides in human milk and bacterial colonization. J Pediatr Gastroenterol Nutr 2000; 30 Suppl 2: S8-17.
25. Moro G, Minoli I, Mosca M, et al. Dosage-related bifidogenic effects of galacto- and fructooligosaccharides in formula-fed term infants. J Pediatr Gastroenterol Nutr 2002; 34: 291-295.
26. Boehm G, Lidestri M, Casetta P, et al. Supplementation of a bovine milk formula with an oligosaccharide mixture increases counts of faecal bifidobacteria in preterm infants. Arch Dis Child Fetal Neonatal Ed 2002; 86: F178-181.
27. Crane J K, Azar S S, Stam A, Newburg D S. Oligosaccharides from human milk block binding and activity of the *Escherichia coli* heat-stable enterotoxin (STa) in T84 intestinal cells. J Nutr 1994; 124: 2358-2364.
28. Cervantes L E, Newburg D S, Ruiz-Palacios G M. a1-2 Fucosylated chains (H-2 and Lewisb) are the main human milk receptor analogs for *Campylobacter*. Pediatr Res 1995; 37: 171A.
29. Shen Z, Warren C D, Newburg D S. High-performance capillary electrophoresis of sialylated oligosaccharides of human milk. Anal Biochem 2000; 279: 37-45.
30. Newburg D, Peterson J, Ruiz-Palacios Q et al. Role of human-milk lactadherin in protection against symptomatic rotavirus infection. Lancet 1998; 351: 1160-1164.
31. Shen Z, Warren C D, Newburg D S. Resolution of structural isomers of sialylated oligosaccharides by capillary electrophoresis. J Chromatogr A 2001; 921: 315-321.
32. Dai D, Nanthkumar N N, Newburg D S, Walker W A. Role of oligosaccharides and glycoconjugates in intestinal host defense. J Pediatr Gastroenterol Nutr 2000; 30: S23-33.
33. Yolken R H, Peterson J A, Vonderfecht S L, Fouts E T, Midthun K, Newburg D S. Human milk mucin inhibits rotavirus replication and prevents experimental gastroenteritis. J Clin Invest 1992; 90: 1984-1991.
34. Newburg D S, Peterson J A, Ruiz-Palacios G M, et al. Role of human-milk lactadherin in protection against symptomatic rotavirus infection. Lancet 1998; 351: 1160-1164.
35. Chaturvedi P, Warren C D, Altaye M, et al. Fucosylated human milk oligosaccharides vary between individuals and over the course of lactation. Glycobiology 2001; 11: 365-372.
36. Henry S, Oriol R, Samuelsson B. Lewis histo-blood group system and associated secretory phenotypes. Vox Sang 1995; 69: 166-182.
37. Koda Y, Tachida H, Pang H, et al. Contrasting patterns of polymorphisms at the ABO-secretor gene (FUT2) and plasma alpha(1,3)fucosyltransferase gene (FUT6) in human populations. Genetics 2001; 158: 747-756.
38. Henry S, Mollicone R, Fernandez P, Samuelsson B, Oriol R, G L. Homozygous expression of a missense mutation at nucleotide 385 in the FUT2 gene associates with the Le(a+b+) partial-secretor phenotype in an Indonesian family. Biochem Biophys Res Commun 1996; 219: 675-678.
39. Newburg D S. Are all human milks created equal? Variation in human milk oligosaccharides. J Pediatr Gastroenterol Nutr 2000; 30: 131-133.
40. Blackwell C C, Jonsdottir K, Hanson M F, Weir D M. Non-secretion of ABO blood group antigens predisposing to infection by *Haemophilus influenzae*. Lancet 1986; 2: 687.
41. Kallenius G, Mollby R, Svenson S B, Winberg J, Hultberg H. Identification of a carbohydrate receptor recognized by uropatlhogenic *Escherichia coli*. Infection 1980; 8: 288-293.
42. Ikehara Y, Nishihara S, Yasutomi H, et al. Polymorphisms of two fucosyltransferase genes (Lewis and Secretor genes) involving type I Lewis antigens are associated with the presence of anti-*Helicobacter pylori* IgG antibody. Cancer Epidemiol Biomarkers Prev 2001; 10: 971-977.
43. Newburg D S, Chaturvedi P, Lopez E L, Devoto S, Gayad A, Cleary T G. Susceptibility to hemolytic-uremic syndrome relates to erythrocyte glycosphingolipid patterns. J Infect Dis 1993; 168: 476-479.

44. Glass R I, Holmgren J, Haley C E, et al. Predisposition for cholera of individuals with O blood group. Possible evolutionary significance. Am J Epidemiol 1985; 121: 791-796.

45. Erney R M, Malone W T, Skelding M B, et al. Variability of human milk neutral oligosaccharides in a diverse population. J Pediatr Gastroenterol Nutr 2000; 30: 181-192.

46. Warren C D, Chaturvedi P, Newburg A R, Oftedal O T, Tilden C D, Newburg D S. Comparison of oligosaccharides in milk specimens from humans and twelve other species. Adv Exp Med Biol 2001; 501: 325-332.

47. Tauxe R V. Epidemiology of *Campylobacter jejuni* infections in the United States and other industrialized nations. In: Nachamkin I, Blaser M J, Tomkins L S, eds. *Campylobacter jejuni* Current Status and Future Trends. Washington, D.C.: American Society for Microbiology, 1992: 9-19.

48. Allos B M. *Campylobacter jejuni* Infections: update on emerging issues and trends. Clin Infect Dis 2001; 32: 1201-1206.

49. Mead P S, Slutsker L, Dietz V, et al. Food-related illness and death in the United States. Emerg Infect Dis 1999; 5: 607-625.

50. Wheeler J G, Sethi D, Cowden J M, et al. Study of infectious intestinal disease in England: rates in the community, presenting to general practice, and reported to national surveillance. The Infectious Intestinal Disease Study Executive. Br J Med 1999; 318: 1046-1050.

51. de Wit M A S, Koopmans M P G, Kortbeek L M, van Leeuwen N J, Vinje J, van Duynhoveri Y T H P. Etiology of gastroenteritis in sentinel general practices in The Netherlands. Clin Infect Dis 2001; 33: 280-288.

52. Shallow R K, Samuel S, McNees A, al. e. Preliminary Food Net data on the incidence of foodborne illnesses. Selected sites, United States 2000. MMWR CDC Surveill Summ 2001; 50: 241-246.

53. CDSC. Trends in selected gastrointestinal infections-2000. Commun Dis Rep CDR Weekly 2001; 10: 8.

54. Havelaar A H, de Wit M A, van Koningsveld R, van Kempen E. Health burden in the Netherlands due to infection with thermophilic *Campylobacter* spp. Epidemiol Infect 2000; 125: 505-522.

55. Calva J J, Ruiz-Palacios G M, Lopez-Vidal A B, Ramos A, Bojalil R. Cohort study of intestinal infection with *campylobacter* in Mexican children. Lancet 1988; 1: 503-506.

56. Albert M J, Farouque A S G, Farouque S M, Sack R B, Mahalanabis D. Case-control study of enteropathogens associated with childhood diarrhea in Dhaka, Bangladesh. J Clin Microbiol 1999; 37: 3458-3464.

57. Smith K E, Besser J M, Hedberg C W, et al. Quinolone-resistant *Campylobacter jejuni* infections in Minnesota, 1992-1998. Investigation Team. N Engl J Med 1999; 340: 1525-1532.

58. Kallenius G, Mollby R, Svensson S B, et al. The Pk antigen as receptor for the haemagglutinin of pyelonephritogenic *Escherichia coli*. FEMS Microbiol Lett 1980; 7: 297.

59. Lomberg H, Leffler H, Svanborg-Eden C. Influence of secretor status on the availability of receptors for attaching *Escherichia coli* on human uroepithelial cells. In: Lark D L, ed. Protein-Carbohydrate Interactions in Biological Systems. London: Academic Press, 1986: 235-238.

60. Blackwell C C, May S J, Brettle R P, MacCallum C J, Weir D M. Host-parasite interactions underlying non-secretion of blood group antigens and susceptibility to recurrent urinary tract infections. In: Lark D L, ed. Protein-Carbohydrate Interactions in Biological Systems. London: Academic Press, 1986: 229-230.

61. Howie P W, Forsyth J S, Ogston S A, Clark A, du V Florey C. Protective effect of breast feeding against infection. Br Med f 1990; 300: 11-16.

62. Teele D W, Klein J O, Rosner B, Group GBOMS. Epidemiology of otitis media during the first seven years of life in children in Greater Boston: A prospective, cohort study. J Infect Dis 1989; 160: 83-94.

63. Newburg D S. Oligosaccharides and glycoconjugates in human milk: Their role in host defense. J Mammary Gland Biol Neoplasia 1996; 1: 271-283.

64. Ruiz-Palacios G M, Cervantes L E, Newburg D S, Lopez-Vidal Y, Calva J J. In vitro models for studying *Campylobacter jejuni* infections. In: Nachamkin I, Blaser M J, Tomkins L S, eds. *Campylobacter jejuni* Current Status and Future Trends. Washington, D.C.: American Society for Microbiology, 1992: 176-183.

65. Reguigne-Arnould I, Couillin P, Mollicone R, et al. Relative positions of two clusters of human a-L-fucosyltransferases in 19q (FUT1-FUT2) and 19p (FUT6-FUT3-FUT5) within the microsatellite genetic map of chromosome 19. Cytogenet Cell Genet. 1995; 71: 158-162.

66. Bry L, Falk P G, Gordon J L. Genetic engineering of carbohydrate biosynthetic pathways in transgenic mice demonstrates cell cycle-associated regulation of glycoconjugate production in small intestinal epithelial cells. Proc Natl Acad Sci USA 1996; 93: 1161-1166.

67. Parkhill J, Wren B W, Mungall K, et al. The genome sequence of the food-borne pathogen *Campylobacter jejuni* reveals hypervariable sequences. Nature 2000; 403: 665-668.

68. Walker R I, Caldwell M B, Lee E C, Guerry P, Trust T, Ruiz-Palacios G M. Pathophysiology of *Campylobacter enteritis*. Microbiol. Rev 1986; 50: 81-94.

69. van Vliet A H, Ketley J M. Pathogenesis of enteric *Campylobacter infection*. J Appl Microbiol 2001; 90: 45S-56S.

70. Wassenaar T M, Blaser M J. Pathophysiology of *Campylobacter jejuni* infection of humans. Microbes Infect 1999; 1: 1023-1033.

71. Fauchere J L, Rosenau A, Veron M, Moyen E N, Richard S, Pfister A. Association with HeLa cells of *Campylobacter jejuni* and *Campylobacter coli* isolated from human feces. Infect Immun 1986; 54: 283-287.

72. Pei Z, Blaser M J. PEB 1, the major cell-binding factor of *Campylobacter jejuni*, is a homologue of the binding component in Gram negative nutrient transport systems. J Biol Chem 1993; 267: 18717-18725.

73. Pei S, Doye A, Boquet P. Mutation of specific acidic residues of the CNF1 T domain into lysine alters cell membrane translocation of the toxin. Mol Microbiol 2001; 41: 1237-1247.

74. Wooldridge K G, Ketley J M. *Campylobacter*-host cell interactions. Trends in Microbiology 1997; 5: 96-102.

75. Marchant J, Wren B W, Ketley J M. Exploiting genome sequence: prediction for mechanisms of *campylobacter* chemotaxis. Trends Microbiol 2002; 10: 155-159.

76. Hugdahl M B, Beery J T, Doyle M P. Chemotactic behavior of *Campylobacter jejuni*. Infect Immune 1988; 56:1560-1566.

77. Jagannathan A, Constantinidou C H, Pemi C H W. Roles of rpoN, fliA, and flgR in expression of flagella in *Campylobacter jejuni*. J Bacteriol 2001; 183: 2937-2942.

78. Allen K J, Griffiths M W. Effect of environmental and chemotactic stimuli on the activity of the *Campylobacter jejuni* flaA s28 promoter. FEMS Microbiol Lett 2001; 205: 43-48.

79. Szymanski C H M, Burr D H, Guerry P. *Campylobacter* protein glycosylation affects host cell interactions. Infect Immun 2002; 70: 2242-2244.

80. Cinco M, Banfi B, Ruaro E, et al. Evidence for L-fucose (6 deoxy-1-galactopyrasone) mediated adherence of *Campylobacter* spp. to epithelial cells. FEMS Microbiol Lett 1984; 21: 347-351.

81. Prieto P A, Larsen R D, Cho M, et al. Expression of human H-type α1,2-fucosyltransferase encoding for blood group H(O) antigen in Chinese hamster ovary cells. Evidence for preferential fucosylation and truncation of polylactosamine sequences. J Biol Chem 1997; 272: 2089-2097.

82. Prieto P A, Mukeri P, Kelder B, et al. Remodeling of mouse milk glycoconjugates by transgenic expression of a human glycosyltransferase. J Biol Chem 1995; 270: 29515-29519.

83. Barua D, Paguio A S. ABO blood groups and cholera. Ann Hum Biol 1977; 4: 489-492.

84. Levine M M, Nalin D R, Rennels M B, et al. Genetic susceptibility to cholera. Ann Hum Biol 1979; 6: 369-374.

85. Lagos R, Avendano A, Prado V, et al. Attenuated live cholera vaccine strain CVD 103-HgR elicits significantly higher serum vibriocidal antibody titers in persons of blood group O. Infect Immun 1995; 63: 707-709.

86. Hanne L F, Finkelstein R A. Characterization and distribution of the hemagglutinins produced by *Vibrio cholerae*. Infect Immun 1982; 36: 209-214.

87. Holgersson J, Stromberg N, Breimer M E. Glycolipids of human large intestine: difference in glycolipid expression related to anatomical localization, epithelial/non-epithelial tissue and the ABO, Le and Se phenotypes of the donors. Biochimie 1988; 70: 1565-1574.

88. Galvan E M, Roth G A, Monferran C G. Participation of ABH glycoconjugates in the secretory response to *Escherichia coli* heat-labile toxin in rabbit intestine. J Infect Dis 1999; 180: 419-425.

89. Boat T F, Davis J, Stern R C, Cheng P W. Effect of blood group determinants on binding of human salivary mucous glycoproteins to influenza virus. Biochim Biophys Acta 1978; 540: 127-133.

90. Raza M W, Blackwell C C, Molyneaux P, et al. Association between secretor status and respiratory viral illness. Bmj 1991; 303: 815-818.

91. Huang P W, Zhong W M, Morrow A L, Ruiz-Palacios G M, Pickering L I K, Jiang X. Human milk contains elements that block Norwalk-like viruses binding to histo-blood group antigens in saliva. American Society of Virology Meeting.

92. Albermann C, Piepersberg W, Wehmeier U F. Synthesis of the milk oligosaccharide 2'-fucosyllactose using recombinant bacterial enzymes. Carbohydr Res 2001; 334: 97-103.

93. Mattila P. Räbinä J, Hortling S, Helin J, Renkonen R. Functional expression of *Escherichia coli* enzymes synthesizing GDP-L-fucose from inherent GDP-D-mannose in *Saccharomyces cerevisiae*. Glycobiology 2000; 10: 1041-1047.

94. Priem B, Gilbert M, Wakarchuk W W, Heyraud A, Samain E. A new fermentation process allows large-scale production of human milk oligosaccharides by metabolically engineered bacteria. Glycobiology 2002; 12: 235-240.

95. Abe H, Shimma Y-i, Jigami Y In vitro oligosaccharide synthesis using intact yeast cells that display glycosyltransferases at the cell surface through cell wall-anchored protein Pir. Glycobiooogy 2003; 13: 87-95.

96. Cleary T G, Chambers J P, Pickering L K. Protection of suckling mice from heat-stable enterotoxin of *Escherichia coli* by infant formulas. J Pediatr Gastroenterol Nutr 1985; 4: 125-127.

97. Cleary T G, Chambers J P, Pickering L K. Protection of suckling mice from heat-stable enterotoxin of *Escherichia coli* by human milk. J Infect Dis 1983; 148: 1114-1119.

98. Newburg D S, Chaturvedi P, Crane J K, Cleary T G, Pickering L K. Fucosylated oligosaccharide(s) of human milk inhibits stable toxin of *Escherichia coli*. In: Agrawal V P, Sharma C B, Sah A, Zingde M D, eds. Complex Carbohydrates and Advances in Biosciences. Muzaffarnagar, India: Society of Biosciences, 1995: 199-226.

99. Ruvoen-Clouet N, Ganiere J P, Andre-Fontaine G, Blanchard D, Le Pendu J. Binding of rabbit hemorrhagic disease virus to antigens of the ABH histo-blood group family. J Virol 2000; 74: 11950-11954.

100. Huang R T C. Isolation and characterization of the gangliosides of butter milk. Biochim Biophys Acta 1973; 306: 82-84.

101. Lindesmith L, Moe C, LePendu J, Jiang X, Baric R. Determinants of susceptibility and protective immunity to Norwalk virus infection. Annual Meeting of the International Congress of Virology, Paris, France.

102. Morrow A L, Ruiz-Palacios G M, Altaye M, et al. Human milk oligosaccharide homologs of Lewis blood group epitopes and protection against diarrhea in breastfed infants. Glycobiology 2002; 12: Abst 21.

103. Igarashi K. The Koenigs-Knorr reaction. Adv Carbohydr Chem Biochem 1977; 34: 243-283.

104. Paulsen H. Advances in selective chemical syntheses of complex oligosaccharides. Angewandte Chemie International Edition in English 1982; 21: 155-224.

105. Flowers H M. Chemical synthesis of oligosaccharides. Methods Enzymol 1987; 138: 359-404.

106. Lemieux R U, Hendriks K B, Stick R V, James K. Halide ion catalyzed glycosidation reactions. Syntheses of a-linked disaccharides. J Am Chem Soc 1975; 97: 4056-4062.

107. Dejter-Juszynski M, Flowers H M. Studies on the Koenigs-Knorr reaction. Part II. Synthesis of an a-L-linked disaccharide from tri-O-benzyl-a-L-fucopyranosyl bromide. Carbohydr Res 1971; 18: 219-226.

108. Lemieux R U, Driguez H. The chemical synthesis of 2-acetamido-2-deoxy-4-O-(a-L-fucopyranosyl)-3-O-(b-D-galactopyranosyl)-D-glucose. The Lewis a blood-group antigenic determinant. J Am Chem Soc 1975; 97: 4063-4068.

109. Abbas S A, Barlow J J, Matta K L. Synthesis of O-a-L-fucosyranosyl-(1-2)-O-b-D-galactopyranosyl-(1-4)-D-glucosyranose (2'-O-a-L-fucopyranosyl-lactose). Carbohydr Res 1981; 88: 51-60.

110. Hindsgaul O, Norberg T, Pendu J L, Lemieux R U. Synthesis of type 2 human blood-group antigenic determinants. The H, X, and Y haptens and variations of the H type 2 determinant as probes for the combining site of the lectin I of *Ulex europaeus*. Carbohydr Res 1982; 109: 109-142.

111. Nashed M A. Oligosaccharides from "standard intermediates". The 2-amino-2-deoxy-D-galactose analog of the blood-group O(H) determinant, type 2, and its precursors. Carbohydr Res 1983; 114: 53-61.

112. Slife C W, Nashed M A, Anderson L. "Standardized intermediates" for oligosaccharide synthesis. Precursors of b-linked, interior D-galactopyranose units having chain extension at position 4, or positions 4 and 2. Carbohydr Res 1981; 93: 219-230.

113. Nashed M A, Chowdhary M S, Anderson L. "Standardized intermediates" for oligosaccharide synthesis. Precursors of D-galactopyranose residues having chain extension at position 3, or positions 3 and 2. Carbohydr Res 1982; 102: 99-110.

114. Jain R K, Locke R D, Matta K L. A convenient synthesis of O-a-L-fucopyranosyl-(1-2)-O-b-D-galactopyranosyl-(1-4)-D-glucopyranose(2'-O-a-L-fucopyranosyllactose). Carbohydr Res 1991; 212: c1-c3.

115. Liptak A, Jodal I, Nanasi P. Stereoselective ring-cleavage of 3-O-benzyl- and 2,3-di-O-benzyl-4,6-O-benzylidenehexopyranoside derivatives with the LiAlH4-AlC13 reagent. Carbohydr Res 1975; 44: 1-11.

116. Lemieux R U, Driguez H. The chemical synthesis of 2-O-(a-L-fucopyranosyl)-3-O-(a-D-galactopyranosyl)-D-galactose. The terminal structure of the blood-group B antigenic determinants. J Am Chem Soc 1975; 97: 4069-4075.

117. Hanessian S, Banoub J. Chemistry of the glycosidic linkage. An efficient synthesis of 1,2-trans-disaccharides. Carbohydr Res 1977; 53: C13-C16.

118. Hanessian S, Banoub J. Preparation of 1,2-trans-glycosides in the presence of silver trifluoromethanesulfonate. Methods in Carbohydrate Chemistry 1980; 8: 247-250.

119. Banoub J, Bundle D R. 1,2-Orthoacetate intermediates in silver trifluoromethanesulphonate promoted Koenigs-Knorr synthesis of disaccharide glycosides. Can J Chem 1979; 57: 2091-2097.

120. Helferich B, Wedemeyer K-F. Ann 1949; 563: 139-145.

121. Koenigs W, Knorr E. Ueber eimige Derivate des Traubenzuckers und der Galactose. Chemische Berichte 1901; 34: 957-981.

122. Wiesner D A, Sweeley C C. Microscale analysis of glycospingolipids by methanolysis, peracetylation, and gas chromatography. Anal Biochem 1994; 217: 316-322.

123. Levery S B, Hakomori S. Microscale methylation analysis of glycolipids using capillary gas chromatography-chemical ionization mass fragmentography with selected ion monitoring. In: Ginsburg V, ed. Complex Carbohydrates, Part E. New York: Academic Press, 1987: 13-25.

124. McBroom C R, Samanen C H, Goldstein I J. Carbohydrate antigens: Coupling of carbohydrates to proteins by diazonium and phenylisothiocyanate reactions. Complex Carbohydrates, Part B 1972; 28: 212-219.

125. Zopf D A, Tsai C-M, Ginsburg V. Carbohydrate antigens: Coupling of oligosaccharide-phenethylamine derivatives to edestin by diazotization and characterization of antibody specificity by radioimmunoassay. Methods Enzymol 1978; 50: 204-206.

126. Yariv J, Rapport M M, Graf L. The interaction of glycosides and saccharides with antibody to the corresponding phenylazo glycosides. Biochem J 1962; 85: 383-388.

127. Rosenfeld L, Lee Y C. A practical preparation of p-nitrophenyl b-D-mannopyranoside. Carbohydr Res 1976; 46: 155-158.

128. Pazur J H. Affinity chromatography of macromolecular substances on adsorbents bearing carbohydrate ligands. Adv Carbohydr Chem Biochem 1981; 39: 405-447.

129. Newburg D S, Peterson J A, Ruiz-Palacios G M, Matson D O, Morrow A L, Schults J, et al. Role of human-milk lactadherin in protection against symptomatic rotavirus infection. *Lancet* 1998; 351: 1160-4.

130. Newburg D S, Ruiz-Palacios G M, Altaye M, Chaturvedi P, Meinzen-Derr J, Guerrero M L, Morrow A L. Innate protection conferred by fucosylated oligosaccharides of human milk against diarrhea in breastfed infants. *Glycobiology* 2004; 14:253-263.

131. Ruiz-Palacios G M, Cervantes L E, Ramos P, Prieto P A, Newburg D S. *Campylobacter jejuni* binds intestinal H(O) antigen (Fucoα1,2Galβ1,4GlcNAc), and fucosyloligosaccharides of human milk inhibit its binding and infection. *J Biol Chem* 2003; 278:14112-14120.

132. Marionneau S, Ruvoen N, Le Moullac-Vaidye B, Clement M, Cailleau-Thomas A, Ruiz-Palacios G M, et al. Norwalk virus binds to H types ⅓ histo-blood group antigens present on gastro-duodenal epithelial cells of "secretor" individuals. *Gastroenterology* 2002; 122: 1967-77.

133. Huang P, Farkas T, Marionneau S, Zhonig W, Ruvoen-Clouet N, Morrow A L, et al. Noroviruses bind to human ABO, Lewis and secretor histo-blood group antigens: Identification of four distinct strain-specific patterns. J Infect Dis 2003; 188:19-31.

134. Newburg D S, Pickering L K, McCluer R H, Cleary T G. Fucosylated oligosaccharides of human milk protect suckling mice from heat-stabile enterotoxin of *Escherichia coli*. *J Infect Dis* 1990; 162:1075-80.

135. Crane J K, Azar S S, Stam A, Newburg D S. Oligosaccharides from human milk block binding and activity of the *Escherichia coli* heat stable enterotoxin (Sta) in T84 intestinal cells. J Nutr 1994; 124:2358-64.

136. Velazquez F R, Matson D O, Calva J J, Gtierrero M L, Morrow A L, Carter-Campell S, et al. Rotavirus infections in infants as protection against subsequent infections. *N Engl J Med* 1996; 335: 1022-8.

137. Morrow A L, Reves R R, West M S, Guerrero M L, Ruiz-Palacios G M, Pickering L K. Protection against infection with *Giardia lamblia* by breastfeeding in a cohort of Mexican infants. J Pediatr. 1992; 121:363-70.

138. Ruiz-Palacios G M, Calva J J, Pickering L K, Lopez-Vidal Y, Volkow P, Pezzarossi H, West M S. Protection of breast-fed infants against *Campylobacter* diarrhea by antibodies in human milk. J Pediatr 1990; 116:707-13.

139. Farkas T, Jiang X, Guerrero M L, Zhong W, Wilton N, Berke T, et al. Prevalence and genetic diversity of human caliciviruses (HuCVs) in Mexican children. *J Med Virol* 2000; 62: 217-23.

140. Jiang X, Huang P W, Zhong W M, Farkas T, Cubitt D W, Matson D O. Design and evaluation of a primer pair that detects both Norwalk- and Sapporo-like caliciviruses by RT-PCR. *J Virol Methods* 1999; 83: 145-54.

141. Jiang X, Wilton N, Zhong W M, Farkas T, Huang P W, Barrett E, et al. Diagnosis of human caliciviruses by use of enzyme immunoassays. J Infect Dis 2000; 181: S349-59.

142. Ruuska T, Vesikari T. Rotavirus disease in Finnish children: use of numerical scores for clinical severity of diarrhoeal episodes. *Scand J Infect Dis* 1990; 22: 259-67.

143. Chaturvedi P, Warren C D, Ruiz-Palacios G M, Pickering L I, Newburg D S. Milk oligosaccharide profiles by reversed-phase HPLC of their perbenzoylated derivatives. *Anal Biochem* 1997; 251:89-97.

144. Newburg D S, Altaye M, Morrow A L. Is the expression of human milk fucosylated oligosaccharide during the first month of lactation representative of the first year of lactation? *Glycobiology* 2003; 13:885.

145. Glass R I, Holmgren J, Haley C E, Ihan M R, Svennerholm A M, Stoll B J, et al. Predisposition for cholera of individuals with O blood group. Possible evolutionary significance. *Am J Epidemiol* 1985; 121: 791-6.34.

146. Newburg D S, Chaturvedi P, Lopez E L, Devoto S, Fayad A, Cleary T G. Susceptibility to hemolytic-uremic syndrome relates to erythrocyte glycosphingolipid patterns. J Infect Dis 1993; 168: 476-9.

147. Ikehara Y, Nishihara S, Yasutomi H, Kitamura T, Matsuo K, Shimizu N, et al. Polymorphisms of two fucosyltransferase genes (Lewis and Secretor genes) involving type I Lewis antigens are associated with the presence of anti-*Helicobacter pylori* IgG antibody. *Cancer Epidemiol Biomarkers Prev* 2001; 10: 971-7.

148. Hutson A M, Atmar R L, Graham D Y, Estes M K. Norwalk virus infection and disease is associated with ABO histo-blood group type. *J Infect Dis* 2002; 185:1335-7.

149. Boat T F, David J, Stern R C, Cheng P W. Effect of blood group determinants on binding of human salivary mucous glycoproteins to influenza virus. *Biochim Biophys Acta* 1978; 54:127-33.

150. Raza M W, Blackwell C C, Molyneaux P, James V S, Ogilvie M M, Inglis J M, et al. Association between secretor status and respiratory viral illness. *BMJ* 1991; 303:815-8.

151. Ciarlet M, Crawford S E, Estes M K. Differential infection of polarized epithelial cell lines by sialic acid-dependent and sialic-acid independent rotavirus strains. *J Virol* 2001; 75: 11834-50.

152. Endo T, Koizumi S. Large-scale production of oligosaccharides using engineered bacteria. Curr Opin Struct Biol 2000; 10:536-541.

153. Endo T, Koizumi S, Tabata K, Kakita S, Ozaki A. Large-scale production of the carbohydrate portion of the sialyl-Tn epitope, alpha-Neup5Ac-(2-->6)-D-GalpNAc, through bacterial coupling. Carbohydr Res 2001; 330:439-443.

154. Endo T, Koizumi S, Tabata K, Ozalki A. Large-scale production of CMP-NeuAc and sialylated oligosaccharides through bacterial coupling. Appl Microbiol Biotechnol 2000; 53:257-261.

155. Chen X, Zhang J, Kowal P, Liu Z, Andreana P R, Lu Y, Wang P G. Transferring a biosynthetic cycle into a productive *Escherichia coli* strain: large-scale synthesis of galactosides. J Am Chem Soc 2001; 123:8866-8867.

156. Chen X, Liu Z, Zhang J, Zhang W, Kowal P, Wang P G. Reassembled biosynthetic pathway for large-scale carbohydrate synthesis: a-Gal epitope producing 'superbug'. Chembiochem 2002; 3:47-53.

157. Dumon C, Priem B, Martin S L, Heyraud A, Bosso C, Samain E. In vivo fucosylation of lacto-N-neotetraose and lacto-N-neohexaose by heterologous expression of *Helicobacter pylori* alpha-1,3 fucosyltransferase in engineered *Escherichia coli*. Glycoconj J 2001; 18:465-474.

158. Priem B, Gilbert M, Wakarchuk W W, Heyraud A, Samain E. A new fermentation process allows large-scale production of human milk oligosaccharides by metabolically engineered bacteria. Glycobiology 2002; 12:235-240.

159. Samain E, Chazalet V, Geremia R A. Production of O-acetylated and sulfated chitooligosaccharides by recombinant *Escherichia coli* strains harboring different combinations of nod genes. J Biotechnol 1999; 72:33-47.

160. Luhn K, Wild M K, Eckhardt M, Gerardy-Schahn R, Vestweber D. The gene defective in leukocyte adhesion deficiency II encodes a putative GDP-fucose transporter. Nat Genet. 2001; 28:69-72.

161. Ishida N, Kawakita M. Molecular physiology and pathology of the nucleotide sugar transporter family (SLC35). Pflugers Arch 2004; 447:768-775.

162. Wu B, Zhang Y, Wang P G. Identification and characterization of GDP-1-mannose 4,6-dehydratase and GDP-1-fucose synthetase in a GDP-1-fucose biosynthetic gene cluster from *Helicobacter pylori*. Biochem Biophys Res Coimnun 2001; 285:364-371.

163. Shao J, Zhang J, Kowal P, Lu Y, Wang P G. Efficient synthesis of globoside and isoglobside tetrasaccharides by using beta(1-->3) N-acetylgalactosaminyltransferase/UDP-N-acetylglicosamine C4 epimerase fusion protein. Chem Commun (Camb) 2003:1422-1423.

164. Bulik D A, van Ophem P, Manning J M, Shen Z, Newburg D S, Jarroll E L. UDP-N-acetylglucosamine pyrophosphorylase, a key enzyme in encysting *Giardia*, is allosterically regulated. J Biol Chem 2000; 275:14722-14728.

165. Sener K, Shen Z, Newburg D, Jarroll E. Amino sugar phosphate levels in *Giardia* change during cyst wall formation. Microbiology 2004; 150:1225-1230.

166. Hamilton S, Bobrowicz P, Bobrowicz B, Davidson R, Li H, Mitchell T, Nett J, Rausch S, Stadheim T, Wischnewski H, Wildt S, Gemgross T. Production of complex human glycoproteins in yeast. Science 2003; 301:1244-1246.

167. Choi B K, Bobrowicz P, Davidson R C, Hamilton S R, Kung D H, Li H, Miele R G, Nett J H, Wildt S, Gerngross T U. Use of combinatorial genetic libraries to humanize N-linked glycosylation in the yeast *Pichia pastoris*. Proc Natl Acad Sci USA 2003; 100:5022-5027.

168. Nakayama K, Maeda Y, Jigami Y. Interaction of GDP-4-keto-6-deoxymannose-3,5-epimerase-4-reductase with GDP-mannose-4,6-dehydratase stabilizes the enzyme activity for formation of GDP-fucose from GDP-mannose. Glycobiology 2003; 13:673 R-680R.

169. Mattila P, Rabina J, Hortling S, Helin J, Renkonen R. Functional expression of *Escherichia coli* enzymes synthesizing GDP-L-fucose from inherent GDP-D-mannose in *Saccharomyces cerevisiae*. Glycobiology 2000; 10:1041-1047.

170. Gao X D, Dean N. Distinct protein domains of the yeast Golgi GDP-mannose transporter mediate oligomer assembly and export from the endoplasmic reticulum. J Biol Chem 2000; 275:17718-17727.

171. Gao X D, Nishikawa A, Dean N. Identification of a conserved motif in the yeast golgi GDP-mannose transporter required for binding to nucleotide sugar. J Biol Chem 2001; 276:4424-4432.

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating or reducing the risk of infection, the method comprising administering to a subject in need thereof a composition containing (a) a molecule including a fucose group in an α1,3 linkage or an α1,4 linkage to a galactose group, (b) 2'-fucosyllactose (2'FL) or 2'-fucosyl-N-acetyllactosamine (2'FLNAc), and (c) a pharmaceutically acceptable carrier; wherein said composition is not a mammalian milk.

2. The method of claim 1, wherein the molecule includes a fucose group in an α1,3 linkage to a galactose group.

3. The method of claim 2, wherein the composition contains 2'FL.

4. The method of claim 2, wherein the composition contains 2'FLNAc.

5. The method of claim 1, wherein the molecule includes a fucose group in an α1,4 linkage to a galactose group.

6. The method of claim 5, wherein the composition contains 2'FL.

7. The method of claim 5, wherein the composition contains 2'FLNAc.

8. The method of claim 1, wherein the composition contains both 2'FL and 2'FLNAc.

9. The method of claim 8, wherein the molecule includes a fucose group in an α1,3 linkage to a galactose group.

10. The method of claim 8, wherein the molecule includes a fucose group in an α1,4 linkage to a galactose group.

11. The method of claim 1, wherein the composition contains 2'FL covalently attached to a protein or 2'FLNAc covalently attached to a protein.

12. The method of claim 11, wherein the molecule includes a fucose group in an α1,3 linkage to a galactose group.

13. The method of claim 12, wherein the composition contains 2'FL covalently attached to a protein.

14. The method of claim 12, wherein the composition contains 2'FLNAc covalently attached to a protein.

15. The method of claim 11, wherein the molecule includes a fucose group in an α1,4 linkage to a galactose group.

16. The method of claim 15, wherein the composition contains 2'FL covalently attached to a protein.

17. The method of claim 15, wherein the composition contains 2'FLNAc covalently attached to a protein.

18. The method of claim 11, wherein the composition contains 2'FL and 2'FLNAc that are both covalently attached to a protein.

19. The method of claim 18, wherein the molecule includes a fucose group in an α1,3 linkage to a galactose group.

20. The method of claim 18, wherein the molecule includes a fucose group in an α1,4 linkage to a galactose group.

* * * * *

UNITED STATES PATENT AND TRADEMARK OFFICE
CERTIFICATE OF CORRECTION

PATENT NO. : 7,893,041 B2
APPLICATION NO. : 10/581759
DATED : February 22, 2011
INVENTOR(S) : Ardythe L. Morrow et al.

Page 1 of 1

It is certified that error appears in the above-identified patent and that said Letters Patent is hereby corrected as shown below:

At column 1, after the "RELATED APPLICATIONS" paragraph, please insert:

--GOVERNMENT SUPPORT

This invention was made with government support under HD013021 awarded by the National Institutes of Health. The government has certain rights in this invention.--

Signed and Sealed this
Ninth Day of April, 2013

Teresa Stanek Rea
*Acting Director of the United States Patent and Trademark Office*